(12) United States Patent
Sasaki et al.

(10) Patent No.: US 7,678,576 B2
(45) Date of Patent: Mar. 16, 2010

(54) CHEMICAL ANALYSIS APPARATUS AND CHEMICAL ANALYSIS CARTRIDGE

(75) Inventors: Shigeyuki Sasaki, Kasumigaura (JP); Yoshihiro Nagaoka, Ishioka (JP); Noriyo Nishijima, Abiko (JP); Naruo Watanabe, Hitachinaka (JP); Michihiro Saito, Kashiwa (JP); Taisaku Seino, Hitachinaka (JP); Satoshi Takahashi, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 1063 days.

(21) Appl. No.: 11/319,680

(22) Filed: Dec. 29, 2005

(65) Prior Publication Data
US 2006/0159586 A1 Jul. 20, 2006

(30) Foreign Application Priority Data
Jan. 17, 2005 (JP) ............................. 2005-009528

(51) Int. Cl.
*G01N 35/00* (2006.01)
*B01F 15/02* (2006.01)
(52) U.S. Cl. .......................... 436/45; 73/1.87; 366/136; 366/137; 366/220; 422/68.1; 422/72; 422/81
(58) Field of Classification Search ......... 366/136–137, 366/220; 422/63–64, 68.1, 72, 81; 436/45; 73/1.87
See application file for complete search history.

(56) References Cited
U.S. PATENT DOCUMENTS
1,469,370 A 10/1923 Trust et al.
5,242,660 A 9/1993 Hsei (Continued)

FOREIGN PATENT DOCUMENTS
EP 0 965 388 12/1999

(Continued)

OTHER PUBLICATIONS

S. Milind et al., Design and Analysis of a Linear type Electromagnetic Stirrer, Industry Applications Conference 2004,XP010735213, pp. 188-194.

*Primary Examiner*—Tony G Soohoo
*Assistant Examiner*—Robert Eom
(74) *Attorney, Agent, or Firm*—Antonelli, Terry, Stout & Kraus, LLP.

(57) ABSTRACT

The invention provides a chemical analysis apparatus which easily agitates and warms up. A chemical analysis apparatus has a motor, a retaining disc which can be rotated by the motor, a plurality of inspection cartridges which are arranged on the retaining disc, a punching machine for punching the inspection cartridges, a warming apparatus and a detection apparatus. The inspection cartridge includes a container formed by a concave portion and a base plate having a flow path. A cover covering the container and the flow path is installed to the base plate. A liquid solution is moved to the container in an outer peripheral side with respect to a rotation axis from the container in an inner peripheral side with respect to the rotation axis via the flow path, by utilizing a centrifugal force generated on the basis of the rotation of the retaining disc. The inspection cartridge is provided with an agitating means for agitating the liquid solution within the container and a warming means for warming up the liquid solution within the container.

11 Claims, 21 Drawing Sheets

U.S. PATENT DOCUMENTS

| | | |
|---|---|---|
| 6,168,948 B1 | 1/2001 | Anderson et al. |
| 6,593,143 B1 | 7/2003 | Gordon |
| 2002/0097632 A1 * | 7/2002 | Kellogg et al. .............. 366/220 |

FOREIGN PATENT DOCUMENTS

| | | |
|---|---|---|
| EP | 1 464 398 | 10/2004 |
| EP | 1 649 931 | 4/2006 |
| FR | 2 841 158 | 12/2003 |
| JP | 8-288055 | 11/1996 |
| JP | 2001-527220 | 12/2001 |
| JP | 2003-502656 | 1/2003 |
| WO | WO 97/08556 | 3/1997 |

* cited by examiner

CHEMICAL ANALYSIS APPARATUS AND CHEMICAL ANALYSIS CARTRIDGE

BACKGROUND OF THE INVENTION

1. Field of the Invention

The present invention relates to a chemical analysis apparatus and a chemical analysis cartridge which extracts and detects a specific chemical material in a liquid sample.

2. Description of the Prior Art

As a chemical analysis apparatus extracting and analyzing a specific chemical material such as a nucleic acid or the like from a sample including a plurality of chemical materials, an integral type fluid operation cartridge is described in JP-A-2001-527220. The apparatus is structured such that an inner portion of the integral type cartridge is provided with capture constituting parts capturing reagents such as a dissolution fluid, a cleaning fluid, an eluting fluid or the like, and the nucleic acid, the sample including the nucleic acid is injected into the inner portion of the cartridge, the sample and the eluting fluid are thereafter mixed so as to be passed through the capture constituting parts, the cleaning fluid is further passed through the capture constituting parts, the eluting fluid is further passed through the capture constituting parts, and the eluting fluid after passing through the capture constituting parts is brought into contact with a PCR reagent so as to be circulated to a reaction chamber. Further, the contents of heating with using a thin film heater is disclosed as a temperature control means.

Further, in JP-A-2003-502656, there is disclosed an apparatus which is provided with a rotating disc, determines a quantity of a sample by using a centripetal force, and employs a PCR amplifying method. There is disclosed a structure in which a temperature control means for setting to a denaturation temperature, an annealing temperature and an elongation temperature in the PCR amplifying method is used within the rotating disc.

Both of the prior arts described in JP-A-2001-527220 and JP-A-2003-502656 employ a nucleic acid amplifying method in the PCR amplifying method repeating a temperature cycle. In the PCR amplifying method, the nucleic acid is amplified in correspondence to a frequency by repeating temperatures 95, 55 and 72° C. corresponding to one example of the temperature cycle, however, it is not necessary to dose the reagent in the process of the cycle.

On the other hand, it is necessary to add an enzyme under a fixed temperature condition in Nucleic Acid Sequence-Based Amplification (NASBA) method of a fixed temperature nucleic acid amplifying method. Accordingly, it is an important problem to agitate a reaction fluid after adding the enzyme, and it is necessary to consider a problem of the agitation in the case of extracting and amplifying the fluid in accordance with a fluidization within a structure body using a centrifugal force.

BRIEF SUMMARY OF THE INVENTION

An object of the present invention is to provide a chemical analysis apparatus which easily agitates and warms up.

A chemical analysis apparatus has a motor, a retaining disc which can be rotated by the motor, a plurality of inspection cartridges which are arranged on the retaining disc, a punching machine for punching the inspection cartridges, a warming apparatus and a detection apparatus. The inspection cartridge includes a container formed by a concave portion and a base plate having a flow path. A cover covering the container and the flow path is installed to the base plate. A liquid solution is moved to the container in an outer peripheral side with respect to a rotation axis from the container in an inner peripheral side with respect to the rotation axis via the flow path, by utilizing a centrifugal force generated on the basis of the rotation of the retaining disc.

The flow path moving the liquid solution to the container in the outer peripheral side from the container in the inner peripheral side starts from an outer peripheral side end of the container in the inner peripheral side, passes through a return portion extending in the inner peripheral direction and again extending in the outer peripheral direction, and ends in an inner peripheral side end of the container in the outer peripheral side.

The inspection cartridge is provided with an agitating means for agitating the liquid solution within the container and a warming means for warming up the liquid solution within the container.

In accordance with the present invention, it is possible to provide a chemical analysis apparatus which easily agitates and warms up.

Other objects, features and advantages of the invention will become apparent from the following description of the embodiments of the invention taken in conjunction with the accompanying drawings.

DETAILED DESCRIPTION OF THE INVENTION

Figure 1:
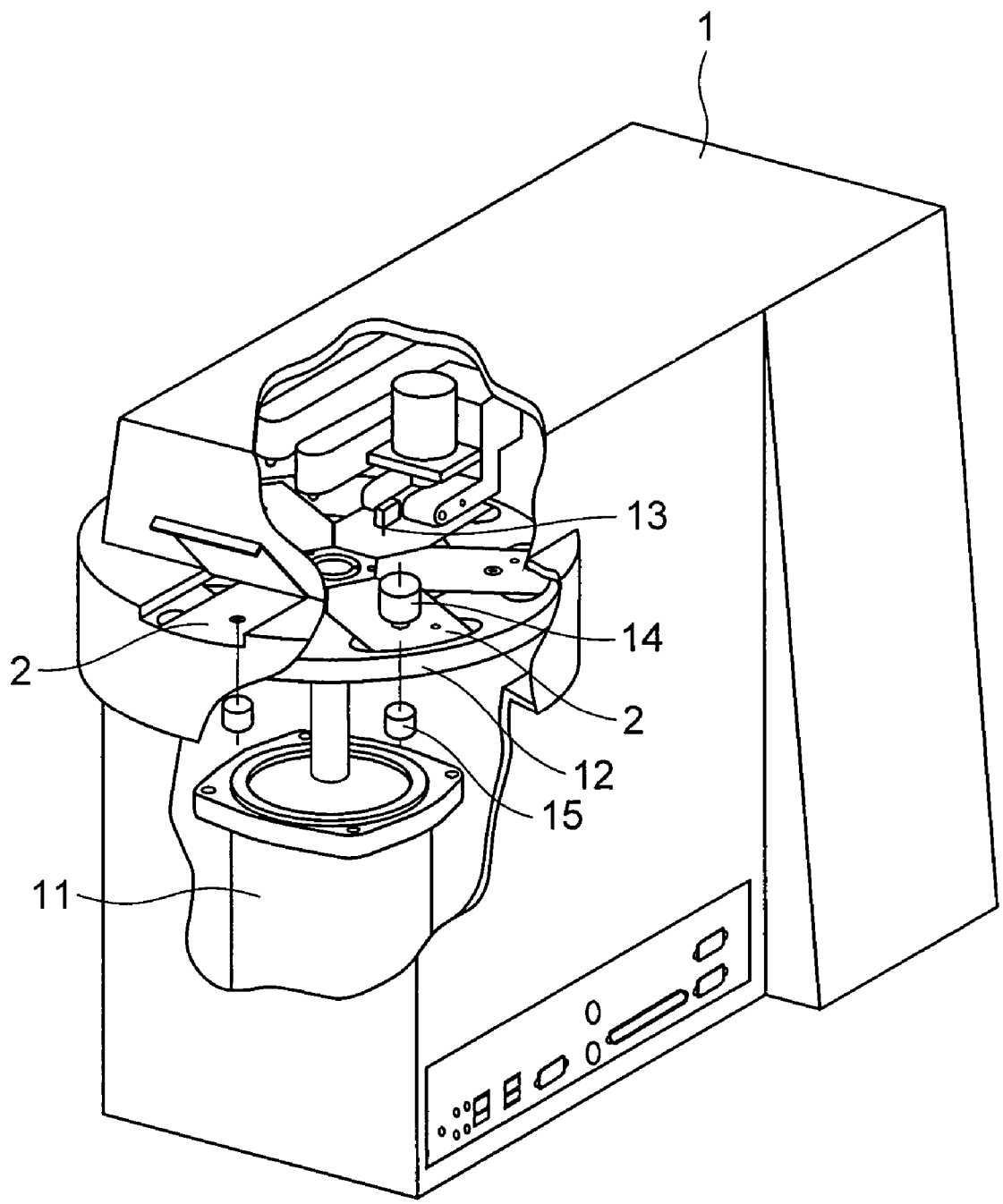
FIG. 1 is a perspective view showing an outer appearance of a chemical analysis apparatus in accordance with the present invention.

FIG. 1 is a view showing an embodiment of a chemical analysis apparatus in accordance with the present invention. A chemical analysis apparatus 1 has a motor 11, a retaining disc 12 which can be rotated by the motor 11, a plurality of inspection cartridges 2 which are arranged on the retaining disc 12, a punching machine 13 for punching the inspection cartridges 2, a warming apparatus 14 and a detection apparatus 15. An operator prepares the inspection cartridge 2 per an inspection item, installs the inspection cartridge 2 to the retaining disc 12, and starts the chemical analysis apparatus 1.

In the chemical analysis apparatus in accordance with the present embodiment, the warming apparatus 14 and the inspection apparatus 15 are respectively provided in different places, however, both elements may be integrally formed and the warming and the inspection may be executed at the same position. Further, the warming apparatus and the inspection apparatus are positioned on an upper surface of the retaining disc 12, however, any one or both of them may be arranged in a lower surface of the retaining disc 12.

Figure 2:
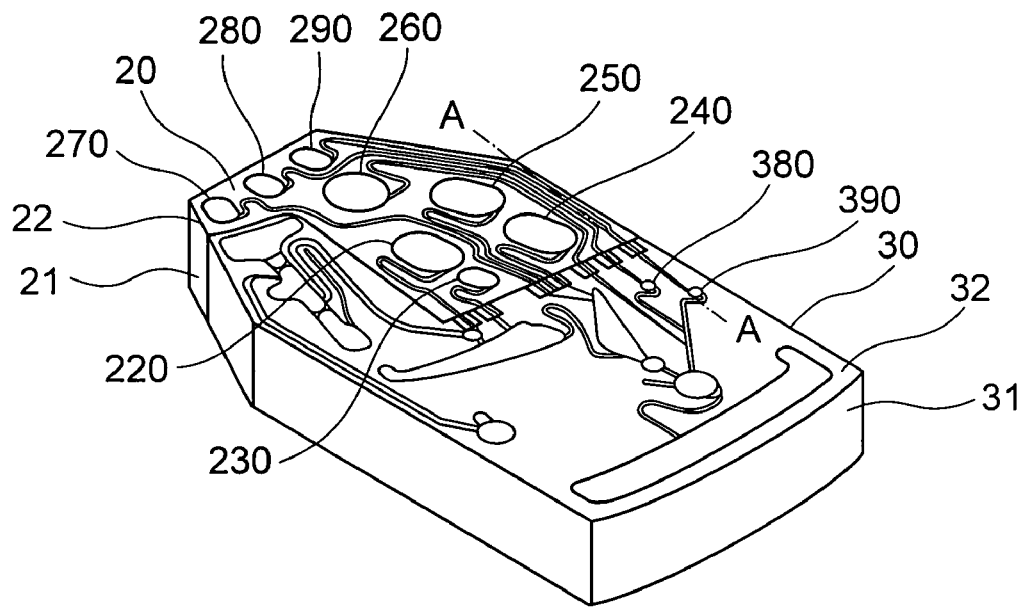
FIG. 2 is a perspective view showing an outer appearance of an inspection cartridge in accordance with the present invention.

FIG. 2 is a perspective view of the inspection cartridge 2. The inspection cartridge 2 is constituted by a thin base plate having an approximately hexagonal shape. Short lines (left upper lines in FIG. 2) of the hexagon are arranged in an inner peripheral side of a center of rotation of the retaining disc, and long lines (right lower lines in FIG. 2) of the hexagon are arranged in an outer peripheral side. Accordingly, the short line side of the hexagon is called as an inner peripheral side, and the long line side of the hexagon is called as an outer peripheral side. A segment connecting the inner peripheral side and the outer peripheral side is called as a radial direction.

The inspection cartridge 2 in accordance with the present embodiment is constituted by a first portion 20 and a second portion 30, and both are connected to each other by joint portions. The first portion 20 of the inspection cartridge 2 is constituted by a base plate and a cartridge cover 22 which is structured by a film or a thin plate jointed so as to cover an entire of an upper surface of the base plate. In the same manner, the second portion 30 of the inspection cartridge 2 is constituted by a base plate 31 and a cartridge cover 32 which is structured by a film or a thin plate joined so as to cover an entire of an upper surface of the base plate.

Figure 3:
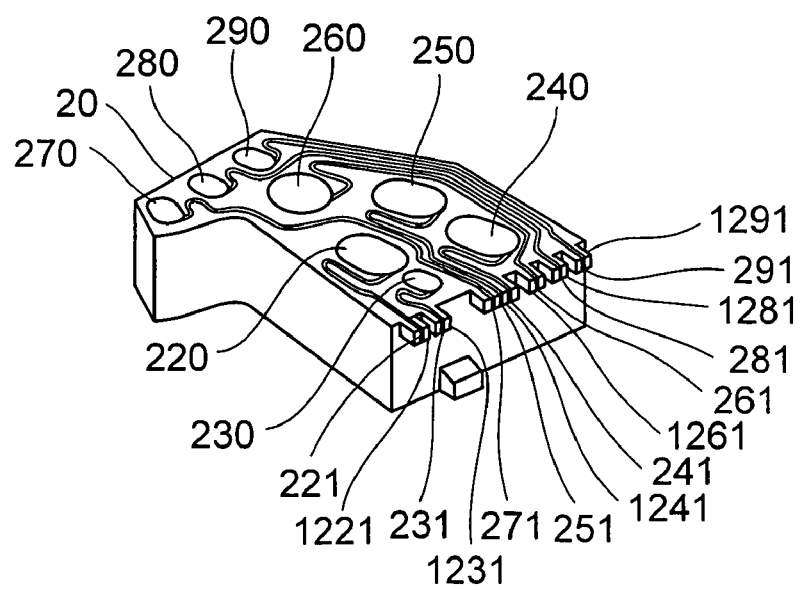
FIG. 3 is a perspective view showing an outer appearance of a first portion of the inspection cartridge in accordance with the present invention.

FIG. 3 shows an outer appearance of the first portion 20 of the inspection cartridge 2. A dissolution fluid container 220, an additional fluid container 230, cleaning fluid containers 240, 250 and 260, an eluting fluid container 270 and detection reagent dissolution fluid containers 280 and 290 are formed in the first portion 20 of the inspection cartridge 2. A predetermined amount of reagent is diluted in these containers. Outlet flow paths 221, 231, 241, 251, 261, 271, 281 and 291 are connected to these containers. Further, the joint portion of the first portion 20 is provided with a projection 1221 including the outlet flow path 221, a projection 1231 including the outlet flow path 231, a projection 1241 including the outlet flow paths 241, 251 and 271, a projection 1261 including the outlet flow path 261, a projection 1281 including the outlet flow path 281 and a projection 1291 including the outlet flow path 291.

Figure 4:
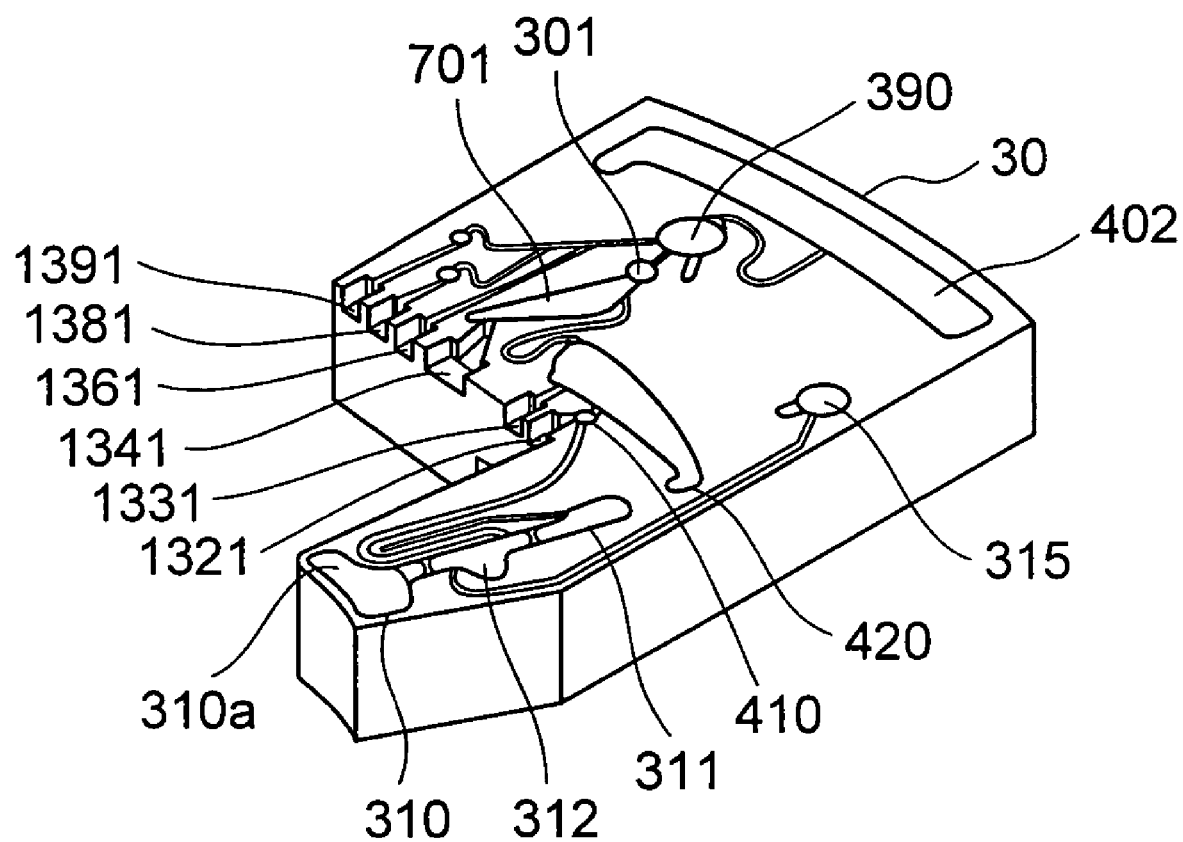
FIG. 4 is a perspective view showing an outer appearance of a second portion of the inspection cartridge in accordance with the present invention.

FIG. 4 shows an outer appearance of the second portion 30 of the inspection cartridge 2. The second portion 30 of the inspection cartridge 2 is provided with a nucleic acid capture portion 301, a sample container 310, a blood cell storage container 311, a blood serum quantitative container 312, a whole blood disposition container 315, an eluting fluid recovery container 390, a waste fluid storage container 402, a mixing container 410, a reaction container 420 and a retention container 701. The nucleic acid capture portion 301 has a porous material such as a quartz or a glass, a fiber filter or the like. Flow paths are connected to these containers. Further, the joint portion of the second portion is provided with concave portions 1321, 1331, 1341, 1361, 1381 and 1391 including these flow paths. A shape of a convex portion of the first portion 20 and a shape of a concave portion of the second portion 30 correspond to each other.

The containers and the flow paths formed in the inspection cartridge 2 correspond to concave portions formed in an upper surface of the base plate. A depth of the flow path is smaller than a depth of the container.

Figure 5A:
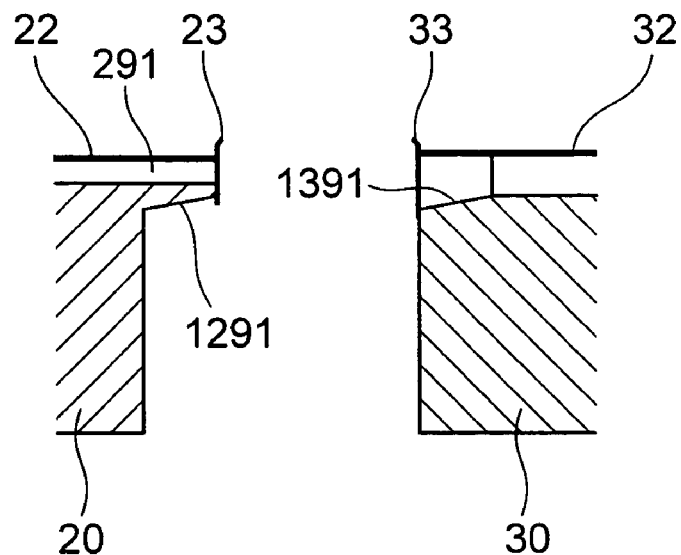
FIGS. 5A and 5B are explanatory views for explaining a method of assembling two portions of the inspection cartridge in accordance with the present invention.
Figure 5B:
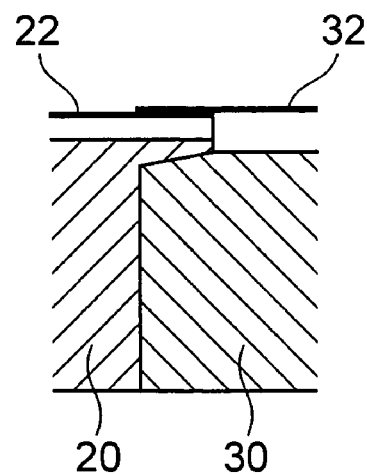

FIG. 5A shows a cross sectional structure at a time of cutting the inspection cartridge along a line A-A portion in FIG. 2 and separating the first portion 20 and the second portion 30, and FIG. 5B shows a cross sectional structure at a time of combining the first portion 20 and the second portion 30. As shown in FIG. 5A, end surfaces of the convex portions 1221, 1231, 1241, 1261, 1281 and 1291 of the joint portion of the first portion 20 in the inspection cartridge 2 are covered by a protection sheet 23. In the same manner, end surfaces of the concave portions 1321, 1331, 1341, 1361, 1381 and 1391 of the joint portion of the second portion 30 in the inspection cartridge 2 are covered by a protection sheet 33. Accordingly, the containers, the flow paths and the like formed in the first portion 20 and the second portion 30 of the inspection cartridge 2 are sealed by the cartridge covers and the protection sheets.

In the case of assembling the first portion 20 and the second portion 30 of the inspection cartridge 2, the protection sheets 23 and 33 in the joint portion are first peeled. Next, the joint portions of the first portion 20 and the second portion 30 are engaged with each other in such a manner that the convex portion of the joint portion of the first portion 20 engages with the concave portion of the joint portion of the second portion 30. As shown in FIG. 5B, an edge of the cartridge cover 22 of the first portion 20 and an edge of the cartridge cover 32 of the second portion 30 are sealed by an adhesive agent or a seal agent. Accordingly, the containers, the flow path and the like of the inspection cartridges form a sealed space.

In the present embodiment, in the inspection cartridge 2, the convex portion of the joint portion of the first portion 20 is formed in such a manner as to include the flow path, and the concave portion of the joint portion of the second portion 30 is formed in such a manner as to include the flow path. Accordingly, the flow path of the first portion 20 and the flow path of the second portion 30 are connected on the basis of an engagement between the convex portion and the concave portion, and the liquid solution does not leak out in the joint portion. In other words, the convex portion of the joint portion of the first portion 20 and the concave portion of the joint portion of the second portion 30 have a positioning function. In this case, the convex portion is provided in the joint portion of the first portion 20 of the inspection cartridge 2, and the concave portion is provided in the joint portion of the second portion 30, however, the structure may be made such that the concave portion is provided in the joint portion of the first portion 20 of the inspection cartridge 2, and the convex portion is provided in the joint portion of the second portion 30.

In the present embodiment, the reagent or the liquid solution is moved between two containers connected to each other by the flow path, by utilizing the centrifugal force. First, the cartridge cover covering two containers is punched, and two containers are left open to an atmospheric pressure. Next, the reagent or the liquid solution within the container moves to the container in the outer peripheral side from the container in the inner peripheral side on the basis of an operation of the centrifugal force, by rotating the retaining disc 12. A predetermined process can be executed by sequentially repeating the operation mentioned above.

Figure 6:
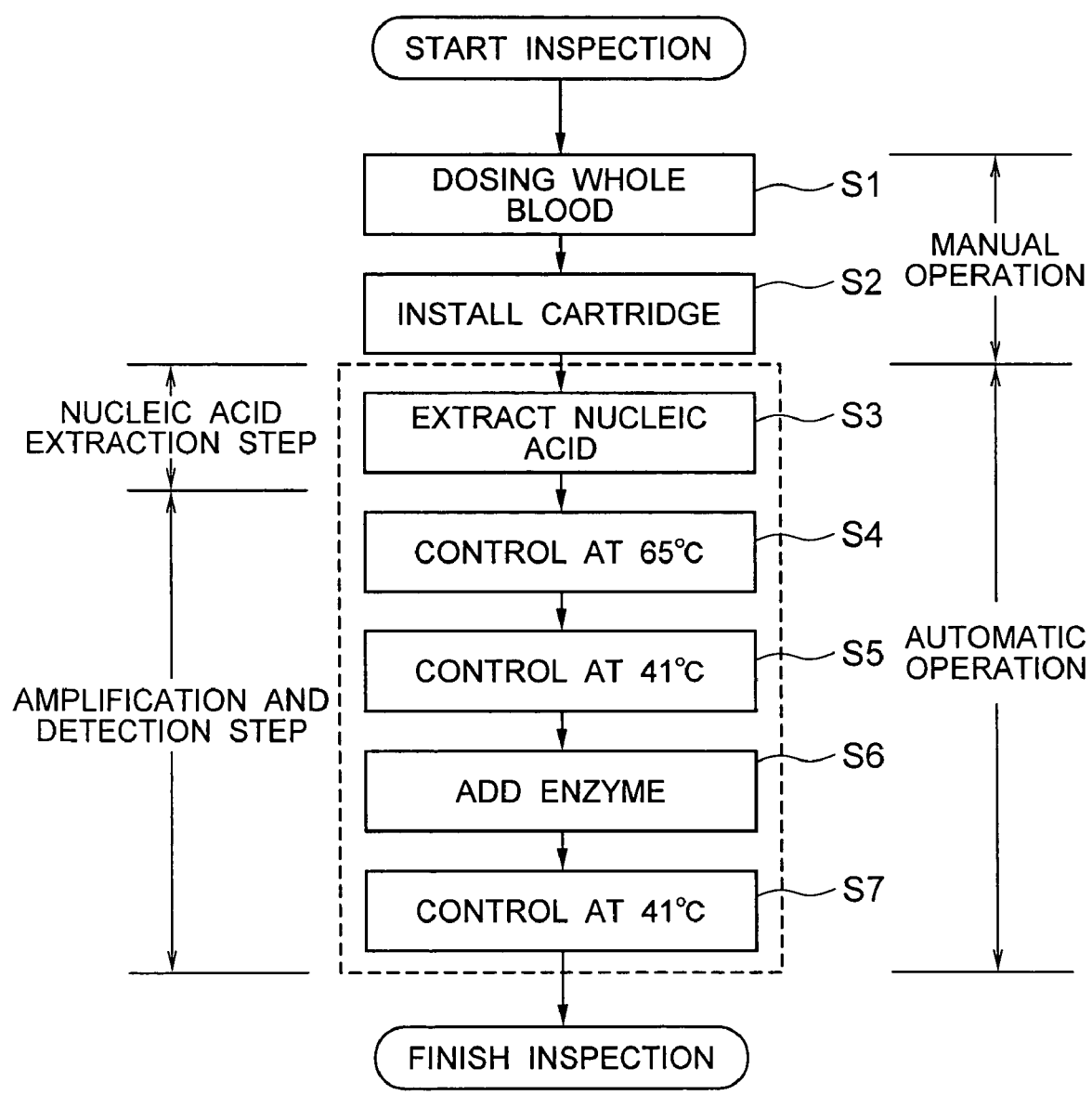
FIG. 6 is an explanatory view for explaining an outline of an operating procedure in the case of executing an extraction process of a virus nucleic acid from a whole blood by using the chemical analysis apparatus in accordance with the present invention.

A description will be given of an extraction and an analyzing operation of a virus nucleic acid in the case of using a whole blood as a sample with reference to FIG. 6. In a step S1, a whole blood dosing is executed. An operator first injects the whole blood collected by a vacuum blood collection tube or the like into the sample container 310 from a sample injection port 310a of the first portion 30 of the inspection cartridge shown in FIG. 4. Next, the protection sheets 23 and 33 are peeled as shown in FIG. 5A, and the first portion 20 of the inspection cartridge is installed to the second portion 30 of the first portion 20 as shown in FIG. 5B. In a step S2, a necessary number of inspection cartridges are installed to the retaining disc 12.

The chemical analysis apparatus 1 is activated as follows, and there are executed a nucleic acid extraction step of extracting a nucleic acid from the whole blood, and an amplification and detection step of amplifying and detecting a gene of the virus. A description will be given of an example of a hepatitis C inspection in accordance with an NASBA method. The nucleic acid is extracted in a step S3, and a reaction fluid in which the sample after extracting the nucleic acid and the amplification fluid are mixed is retained at 65° C. for about 5 minute in a step S4. The temperature is descended to 41° C. corresponding to an enzyme proper temperature in a step S5. The enzyme is added in a step S6, and is retained at 41° C. for about 90 minute in a step S7. An amount of gene of the virus can be evaluated by measuring an amount of fluorescence at this time in real time.

Figure 7:
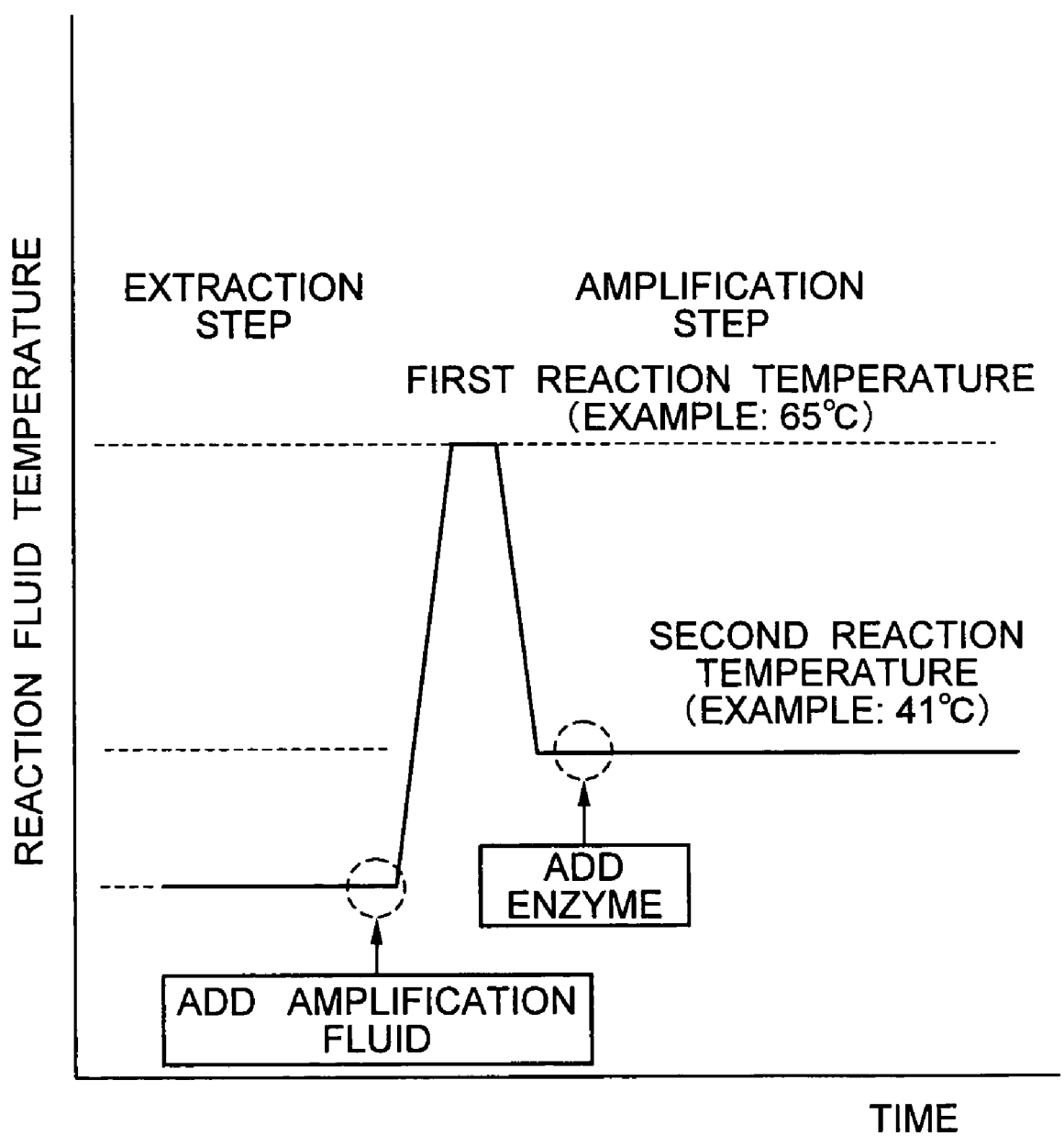
FIG. 7 is an explanatory view for explaining an agitating timing in the case of executing the extraction process of the virus nucleic acid from the whole blood by using the chemical analysis apparatus in accordance with the present invention.

Next, a description will be given of a timing of the agitation with reference to FIG. 7. In FIG. 7, a horizontal axis corresponds to a time, and a vertical axis corresponds to a reaction fluid temperature. The extraction step of the nucleic acid is executed at a room temperature. The agitation is executed in the amplification step next to the extraction step. First, the amplification fluid is added to the nucleic acid extracted in the extraction step and is agitated. Next, it is retained at 65° C. corresponding to a first reaction temperature for 5 minute. The temperature is controlled to the enzyme proper temperature 41° C. corresponding to a second reaction temperature, and an enzyme fluid is added and agitated. In other words, the agitation is executed at a time of adding the amplification reagent and at a time of adding the enzyme.

Figure 8:
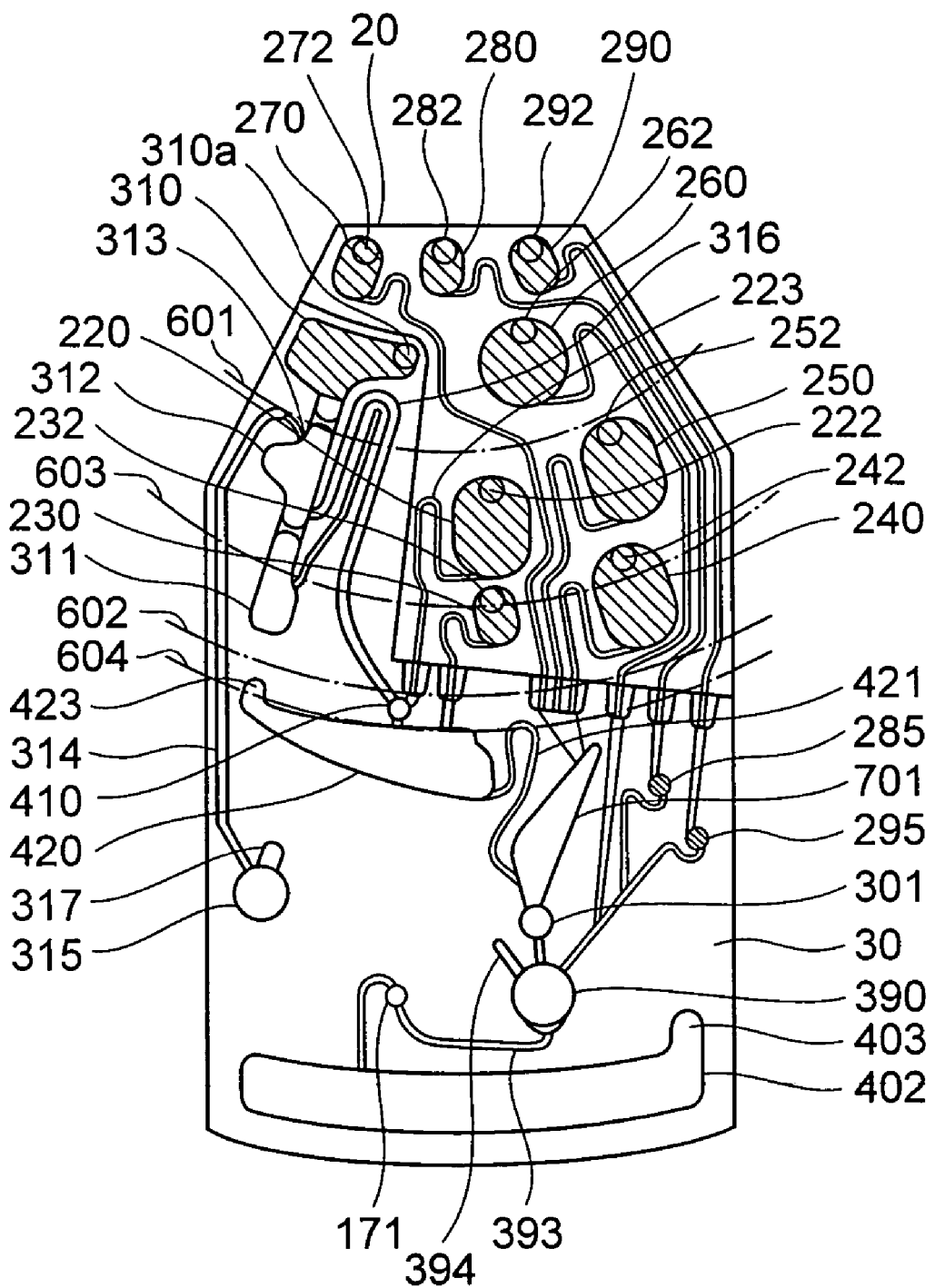
FIG. 8 is an explanatory view of an operation of the inspection cartridge in accordance with the present invention.

A description will be given of a fluid state of the fluid in the inspection cartridge with reference to FIG. 8. The dissolution fluid for dissolving a membrane protein of the virus in the blood serum so as to elute the nucleic acid is dosed in the dissolution fluid container 220. The dissolution fluid serves so as to dissolve the protein corresponding to the membrane of the virus or a bacteria in the blood serum, however, promotes an adsorption of the nucleic acid to the nucleic acid capture portion 301. The dissolution fluid may be constituted, for example, by a guanidine hydrochloride for eluting and adsorbing DNA, and a guanidine thiocyanate for eluting and absorbing RNA.

An additional fluid for supplementing the dissolution fluid is dosed to the additional fluid container 230. The additional fluid may be constituted, for example, by the dissolution fluid itself. A first cleaning fluid for cleaning an unnecessary component such as the protein or the like attached to the nucleic acid capture portion 301 is dosed to the first cleaning fluid container 240. The first cleaning fluid may be constituted, for example, the dissolution fluid or a fluid in which a salt concentration of the dissolution fluid is reduced. A second cleaning fluid for cleaning an unnecessary component such as a salt or the like attached to the nucleic acid capture portion 301 is dosed to the second cleaning fluid container 250. The second cleaning fluid may be constituted, for example, by an ethanol water solution.

A third cleaning fluid for cleaning the component such as the salt or the like attached to the eluting fluid recovery container 390 is dosed to the third cleaning fluid container 260. The third cleaning fluid may be constituted, for example, by a sterilized water or a water solution in which pH is adjusted from 7 to 9. The dissolution fluid for eluting the nucleic acid from the nucleic acid capture portion 301 is dosed to the dissolution fluid container 270. The eluting fluid may be constituted by the sterilized water or the water solution in which pH is adjusted from 7 to 9.

A first detection reagent and a second detection reagent in a dried state are stored respectively in a first detection reagent container 285 and a second detection reagent container 295. All the components contained in two reagents may be stored as one kind of reagent in the second detection reagent container 295. In this case, the first detection reagent container 285 is not necessary.

The detection reagent can be stored at a room temperature or under refrigeration for a long period by being stored in the dried state. However, in the case that it is not necessary to store in the dried state, the detection reagent may be previously dissolved in the dissolution fluid.

The dissolution fluid for dissolving the first detection reagent and the second detection reagent in the dried state is stored in the first detection reagent dissolution fluid container 280 and the second detection reagent dissolution fluid container 290.

Vent holes 222, 232, 242, 252, 262, 272, 282 and 292 are provided in inner peripheral ends of the reagent containers 220, 230, 240, 250, 260, 270, 280 and 290. Vent holes 317, 394, 403 and 423 are provided in inner peripheral ends of the whole blood disposition container 315, the dissolution fluid recovery container 390, the waste fluid storage container 402 and the reaction container 420. These containers are connected to the atmospheric pressure by punching the cover in upper sides of the vent holes.

The sample injection port 310a is provided in the sample container 310. The operator punches the cartridge cover in the upper side of the sample injection port 310a of the inspection cartridge, and injects the whole blood collected by the vacuum blood collection tube or the like into the sample container 310 from the sample injection port 310a.

First, a description will be given of a blood serum separation process. The cover is punched in the upper side of the whole blood disposition container vent hole 317 by the punching machine 13. Accordingly, the whole blood disposition container 315 is connected to the atmospheric pressure via the whole blood disposition container vent hole 317. In this case, the sample container 310 is connected to the atmospheric pressure via the sample injection port 310a. The motor 11 is driven and the retaining disc 12 is rotated. The whole blood within the sample container 310 moves in an outer peripheral direction on the basis of an operation of a centrifugal force, and flows to the blood cell storage container 311 and the blood serum quantitative container 312.

An overflow flow path having a return portion starting from an inner peripheral end of the blood serum quantitative container 312, extending in an inner peripheral direction and again extending in an outer peripheral direction is provided between the blood serum quantitative container 312 and the whole blood disposition container 315. The overflow flow path includes an overflow thin tube flow path 313 in which a cross sectional area is small from the blood serum quantitative container 312 to the return portion, and an overflow thick tube flow path 314 in which a cross sectional area is large from the return portion to the whole blood disposition container 315. In other words, the overflow narrow tube flow path 313 and the overflow thick tube flow path 314 are connected in the return portion. Accordingly, if the blood cell storage container 311 and the blood serum quantitative container 312 are filled with the whole blood, the whole blood flows through the whole blood disposition container 315 via the overflow flow path.

If the retaining disc 12 is continuously rotated, the blood cell moves to the blood cell storage container 311 in the outer peripheral side, and the blood serum leaves in the blood serum quantitative container 312 in the inner peripheral side. In other words, the whole blood is separated into the blood cell and the blood serum. If a blood serum centrifugal separating motion is finished by rotating for a predetermined time, the rotation of the retaining disc 12 is stopped.

A dam is provided between the blood serum quantitative container 312 and the blood cell storage container 311, and the blood cell within the blood cell storage container 311 can not return to the blood serum quantitative container 312.

A blood serum capillary tube 316 having a return portion starting from the outer peripheral end of the blood serum quantitative container 312, extending in the inner peripheral direction and again extending in the outer peripheral direction is provided between the blood serum quantitative container 312 and a mixing container 410.

A part of the blood serum within the blood serum quantitative container 312 moves within the blood serum capillary tube 316 on the basis of a capillary tube force caused by a surface tension, and reaches an inlet of the mixing container corresponding to a boundary between the mixing container 410 and the blood serum capillary tube 316. However, since the cross sectional area is enlarged in the mixing container 410, the capillary tube force is reduced, and the blood serum never mover more. In the same manner, a part of the blood serum within the blood serum quantitative container 312 moves within the overflow narrow tube flow path 313 on the basis of the capillary tube force caused by the surface tension, however, since a cross sectional area is enlarged in the overflow thick tube flow path 314, the capillary tube force is reduced, and the blood serum never moves more. A position 601 in a radial direction shows a liquid surface level in the blood serum quantitative container 312 and the overflow narrow tube flow path 313.

In the present embodiment, the blood serum quantitative container 312 has a function of determining the quantity of a predetermined amount of blood serum. For example, it is assumed that a volumetric capacity of the blood cell storage container 311 is 250 micro liter, and a necessary amount of the blood serum is 200 micro liter. If 500 micro liter of whole blood is dosed to the sample container 310, 50 micro liter of whole blood overflows to the whole blood disposition container 315, and the remaining 450 micro liter of whole blood is separated into the blood serum and the blood cell. 200 micro liter of blood serum among them flows out to the mixing container 410. In the present embodiment, it is possible to obtain 200 micro liter or more of blood serum from 450 micro liter of whole blood. In the case of the whole blood in which a rate of the blood serum is small, it is preferable to make the volumetric capacity of the blood cell storage container large so as to increase the whole blood sample.

Figure 9:
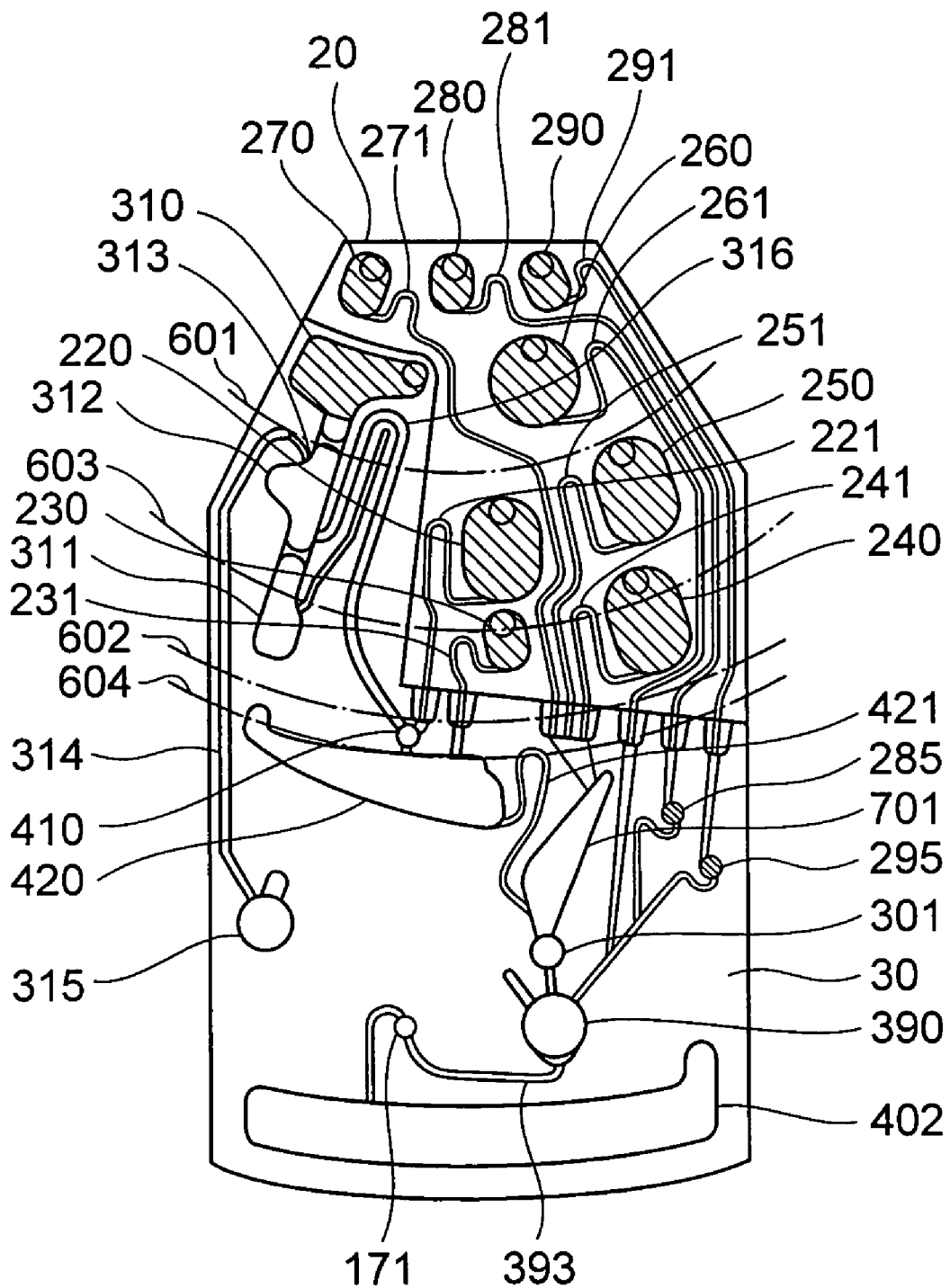
FIG. 9 is an explanatory view of the operation of the inspection cartridge in accordance with the present invention.

As shown in FIG. 9, the outlet flow paths 221, 231, 241, 251, 261, 271, 281 and 291 provided in the outer peripheral side of the reagent containers 220, 230, 240, 250, 260, 270, 280 and 290. The return portion starting from the outer peripheral end of the reagent container, returning to the inner peripheral side and thereafter extending to the outer peripheral side is formed in the outlet flow path.

Since the cartridge covers 22 and 32 are installed to the upper surface of the inspection cartridge, the reagent containers 220, 230, 240, 250, 260, 270, 280 and 290 and the outlet flow paths 221, 231, 241, 251, 261, 271, 281 and 291 are sealed until the cartridge cover 22 is punched at the position of the vent hole, so that no air flows therein. However, a small amount of air sealed at a time of installing the cartridge cover exists in the reagent containers and the outlet flow paths. If the centrifugal force is applied, each of the reagents moves to the outer peripheral side of the reagent container and is pushed within the outlet flow path. However, a small amount of air injected into the reagent container at an early stage is expanded, and a negative pressure is generated within the reagent container. The negative pressure balances with the centrifugal force, and the reagent can not flow out from the reagent container.

If the rotational speed is increased and the centrifugal force becomes large, the pressure within the reagent container is further lowered. If the pressure becomes equal to or less than a saturated vapor pressure of the reagent, bubbles are generated. Accordingly, the negative pressure is reduced, and the balance with the centrifugal pressure is broken. However, in the present embodiment, since the return portion returning to the inner peripheral side is provided in the outlet flow paths 221, 231, 241, 251, 261, 271, 281 and 291 of the respective reagent containers, it is possible to suppress the reduction of the negative pressure within the reagent container and it is possible to prevent the reagent from flowing out from the outlet flow paths, even in the case that the centrifugal force becomes large.

The cartridge cover is punched at the position of the vent hole in each of the reagent containers by the punching machine 13, and each of the reagent containers is connected to the atmospheric pressure. Each of the reagents is fluidized on the basis of the centrifugal force by rotating the retaining disc by means of the motor 11.

Next, a description will be given of the mixing step. The cartridge cover 22 is punched at the position of the vent hole 222 of the dissolution fluid container 220 by the punching machine 13. The cartridge cover 32 is punched at the position of the vent hole 423 of the reaction container 420. Accordingly, the dissolution fluid container 220 and the reaction container 420 are connected to the atmospheric air.

The retaining disc 12 is rotated by driving the motor 11. The dissolution fluid within the dissolution fluid container 220 is fluidized to the outer peripheral side on the basis of the operation of the centrifugal force, and moves to the reaction container 420 via the dissolution fluid container outlet flow path 221 having the return portion, and the mixing container 410.

Since the radial position of the outlet of the dissolution fluid container 220 exists in the inner peripheral side of a radial position 602 of the inlet of the mixing container 410, all the dissolution fluid within the dissolution fluid container 220 flows out to the mixing container 410 on the basis of a siphon effect.

The radial position passing through the connection position between the blood serum quantitative container 312 ad the blood serum capillary tube 316 exists in an inner peripheral side of the radial position 602 of the inlet of the mixing container. Accordingly, all of the blood serum existing in the inner peripheral side of the connection position in the blood serum within the blood serum quantitative container 312 flows out to the mixing container 410 on the basis of a siphon effect. The dissolution fluid and the blood serum flowing out to the mixing container 410 move to the reaction container 420. The blood serum and the dissolution fluid are mixed and reacted within the reaction container 420.

The mixing container 410 corresponds to a space for mixing the dissolution fluid and the blood serum, however, may be provided with a member for promoting the mixing between the blood serum and the dissolution fluid. The member for promoting the mixing includes a porous filter made of a resin, a glass, a paper or the like, a fiber, a protruding material such as a silicone, a metal or the like manufactured in accordance with an etching, a machine work or the like, and the like.

A reaction container outlet flow path 421 having a return portion starting from an outer peripheral end of the reaction container 420, extending in the inner peripheral direction and again extending in the outer peripheral direction is provided between the reaction container 420 and the retaining container 701. During the rotation, a liquid surface level within the reaction container 420 exists in the outer peripheral side of a radial position 604 of an innermost peripheral end of the return portion of the reaction container outlet flow path 421. Accordingly, the mixed fluid within the reaction container 420 never moves to the retaining container 701 over the return portion of the reaction container outlet flow path 421. During the rotation, the mixed fluid is retained in the reaction container 420.

If the motor 11 is rotated for a predetermined time and the mixing process between the blood serum and the dissolution fluid is finished, the motor 11 is stopped, and the rotation of the retaining disc 12 is stopped.

In this case, the mixing container 410 has a function of preventing the mixed fluid within the reaction container 420 from flowing out on the basis of the capillary tube force, at a time when the rotation of the retaining disc is stopped. In other words, when the mixed fluid within the reaction container 420 flows in the direction of the mixing container 410 on the basis of the capillary tube force, the cross sectional area of the mixing container 410 is large. Accordingly, the capillary tube force is reduced and the mixed fluid can not move forward more.

Next, a description will be given of the nucleic acid capturing step. As shown in FIG. 9, the additional fluid container outlet flow path 231 having the return portion starting from the outer peripheral end of the additional fluid container 230, extending in the inner peripheral direction and again extending in the outer peripheral direction is provided between the additional fluid container 230 and the reaction container 420.

The cartridge cover 22 is punched at the position of the vent hole 232 of the additional fluid container 230 by the punching machine 13, and the additional fluid container 230 is connected to the atmospheric pressure. The cartridge cover 32 is punched at the position of the vent hole 394 of the eluting fluid recovery container 390, and the eluting fluid recovery container 390 is connected to the atmospheric pressure. The cartridge cover 32 is punched at the position of the vent hole 403 of the waste fluid storage container 402, and the waste fluid storage container 402 is connected to the atmospheric pressure.

The motor 11 is driven and the retaining disc 12 is rotated. The additional fluid within the additional fluid container 230 moves to the reaction container 420 via the additional fluid container outlet flow path 231 on the basis of the operation of the centrifugal force. Accordingly, the liquid surface level of the mixed fluid within the reaction container 420 moves in the inner peripheral direction. If the liquid surface of the mixed fluid reaches the position 604 of the innermost peripheral portion of the reaction container outlet flow path 421, the mixed fluid flows out over the return portion of the reaction container outlet flow path 421, and flows into the nucleic acid capture portion 301.

In the case that a wet property of the mixed fluid between the blood serum and the dissolution fluid with respect to the wall surface is good, there is a case that the mixed fluid flows backward within the reaction container outlet flow path 421 on the basis of the capillary tube phenomenon even in the case that the centrifugal force is not applied. In the case mentioned above, the additional fluid is not necessary.

The mixed fluid introduced to the nucleic acid capture portion 301 moves in the outer peripheral direction on the basis of the operation of the centrifugal force, and passes through the nucleic acid capture portion 301. If the mixed fluid passes through the nucleic acid capture portion, the nucleic acid in the mixed fluid is captures by the nucleic acid capture portion 301, and the remaining waste fluid flows into the eluting fluid recovery container 390.

After the nucleic acid capture process is executed, a description will be given next of the cleaning step. The first cleaning fluid contained outlet flow path 241 connected to the first cleaning fluid container 240, the second cleaning fluid container outlet flow path 251 connected to the second cleaning fluid container 250, and the eluting fluid container outlet flow path 271 connected to the eluting fluid container 270 flow together in the retaining container 701. The third cleaning fluid container outlet flow path 261 connected to the third cleaning fluid container 260 is connected to the eluting fluid recovery container 390. The first detection reagent dissolution fluid container outlet flow path 281 connected to the first detection reagent dissolution fluid container 280 is connected to the eluting fluid recovery container 390 via the first detection reagent container 285 storing the first detection reagent. The second detection reagent dissolution fluid container outlet flow path 291 connected to the second detection reagent dissolution fluid container 290 is connected to the eluting fluid recovery container 390 via the second detection reagent container 295 storing the second detection reagent. The waste fluid flow path 393 having the return portion starting from the outer peripheral end of the eluting fluid recovery container 390, extending in the inner peripheral direction and again extending in the outer peripheral direction is provided between the eluting fluid recovery container 390 and the waste fluid storage container 402. A capillary tube valve 171 is provided in the middle of the waste fluid flow path 393, and will be described later with reference to FIGS. 12A and 12B.

A description will be given of the cleaning step. The cleaning step includes first, second and third cleaning steps. First, a description will be given of the first cleaning step. The motor 11 is stopped, and the cartridge cover 22 is punched at the position of the vent hole 242 of the first cleaning fluid container 240 by the punching machine 13. Accordingly, the first cleaning fluid container 240 is connected to the atmospheric pressure. When the motor 11 is rotated, the first cleaning fluid flows into the nucleic acid capture portion 301 from the first cleaning fluid container 240 via the first cleaning fluid container outlet flow path 241 and the retaining container 701 on the basis of the operation of the centrifugal force, and cleans the unnecessary component such as the protein or the like attached to the nucleic acid capture portion 301. The waste fluid after cleaning flows out to the waste fluid storage container 402 via the eluting fluid recovery container 390 and the waste fluid flow path 393.

Next, a description will be given of the second cleaning step. The motor 11 is stopped, and the cartridge cover 22 is punched at the position of the vent hole 252 of the second cleaning fluid container 250 by the punching machine 13. Accordingly, the second cleaning fluid container 250 is connected to the atmospheric pressure. When the motor 11 is rotated, the second cleaning fluid flows into the nucleic acid capture portion 301 from the second cleaning fluid container 250 via the second cleaning fluid container outlet flow path 251 and the retaining container 701 on the basis of the operation of the centrifugal force, and cleans the unnecessary component such as the protein or the like attached to the nucleic acid capture portion 301. The waste fluid after cleaning flows out to the waste fluid storage container 402 via the eluting fluid recovery container 390.

A description will be given of the third cleaning step. The motor 11 is stopped, and the cartridge cover 22 is punched at the position of the vent hole 262 of the third cleaning fluid container 260 by the punching machine 13. Accordingly, the third cleaning fluid container 260 is connected to the atmospheric pressure. When the motor 11 is rotated, the third cleaning fluid flows into the eluting fluid recovery container 390 from the third cleaning fluid container 260 on the basis of the operation of the centrifugal force, and cleans the component such as the salt or the like attached to the eluting fluid recovery container 390. The waste fluid after cleaning flows out to the waste fluid storage container 402.

A description will be given of the eluting step. The motor 11 is stopped, and the cartridge cover 22 is punched at the position of the vent hole 272 of the eluting fluid container 270 by the punching machine 13. Accordingly, the eluting fluid container 270 is connected to the atmospheric pressure. When the motor 11 is rotated, the eluting fluid flows into the nucleic acid capture portion 301 from the eluting fluid container 270 via the outlet flow path 271 and the retaining container 701 on the basis of the operation of the centrifugal force. The nucleic acid captured by the nucleic acid capture portion 301 is eluted by the eluting fluid. The eluting fluid including the eluted nucleic acid flows into the eluting fluid recovery container 390 from the nucleic acid capture portion 301. A volumetric capacity of the eluting fluid in the eluting fluid container 270 is equal to smaller than the volumetric capacity of the eluting fluid recovery container 390. Accordingly, the eluting fluid flowing into the eluting fluid recovery container 390 is retained in the eluting fluid recovery container 390.

A description will be given of the amplification step. The amplification step includes first and second amplification steps. A description will be given of the first amplification step. The motor 11 is stopped, and the cartridge cover 22 is punched at the position of the vent hole 282 of the first detection reagent dissolution fluid container 280 by the punching machine 13. Accordingly, the first detection reagent dissolution fluid container 280 is connected to the atmospheric pressure. When the motor 11 is rotated, the first detection reagent dissolution fluid flows into the first detection reagent container 285 from the first detection reagent dissolution fluid container 280 via the outlet flow path 281 on the basis of the operation of the centrifugal force, dissolves the first detection reagent, and flows into the eluting fluid recovery container 390.

The first detection reagent corresponds to an amplification reagent including an internal control and a fluorescence dye. The gene retained in the eluting fluid recovery container 390 is amplified at the same time of being fluorescence labeled by the first detection reagent. If the first detection reagent fluid flows into the eluting fluid recovery container 390, the eluting fluid recovery container 390 is retained at a first reaction temperature, for example, 65° C. for 5 minute by using the warming apparatus 14, and is descended to a second reaction temperature, for example, 41° C. If the temperature reaches the second reaction temperature, the second amplification step is executed.

A description will be given of the second amplification step. The motor 11 is stopped, and the cartridge cover 22 is punched at the position of the vent hole 292 of the second detection reagent dissolution fluid container 290 by the punching machine 13. Accordingly, the second detection reagent dissolution fluid container 290 is connected to the atmospheric pressure. When the motor 11 is rotated, the second detection reagent dissolution fluid flows into the second detection reagent container 295 from the second detection reagent dissolution fluid container 290 via the outlet flow path 291 on the basis of the operation of the centrifugal force, dissolves the second detection reagent, and flows into the eluting fluid recovery container 390.

The second detection reagent corresponds to a reagent including an enzyme. The gene retained in the eluting fluid recovery container 390 is amplified by the second detection reagent. If the second detection reagent fluid flows into the eluting fluid recovery container 390, the eluting fluid recovery container 390 is retained at a second reaction temperature 41° C. for 90 minute by using the warming apparatus 14.

In the second amplification step, the detection apparatus 15 is moved below the eluting fluid recovery container 390 serving as an inspection container, and each of a fluorescence amount of a target nucleic acid and an internal control nucleic acid is detected.

The internal control corresponds to a nucleic acid the quantity of which is previously determined, or a composition containing the nucleic acid, and executes an extraction, an amplification and a detection by using the same condition and apparatus as the condition and the apparatus used for extracting, amplifying and detecting the target nucleic acid in the blood serum.

Accordingly, in the case that a signal of a predetermined fluorescence, absorption or the like is obtained from the detection-result of the internal control, it is possible to assume that the inspection cartridge and the inspection apparatus function normally, and the extraction, amplification and detection steps are executed normally. Therefore, in this case, it is possible to employ the fluorescence amount of the target nucleic acid as a normal measured value. On the contrary, in the case that a signal strength of the detection result of the internal control is lower than the predetermined value or is not absolutely detected, it is possible to judge that the inspection cartridge or the inspection apparatus does not function normally. Alternatively, it is possible to quantitatively evaluate the concentration of the target nucleic acid by comparing the detection signal of the target nucleic acid with the detection signal of the internal control the quantity of which is previously determined.

In accordance with the present invention, the dosing operation of the reagent is not necessary, and a contamination of the reagent is not generated due to an imperfect work. Further, it is not necessary that a valve for controlling a fluidization of each of the reagents is provided in the middle of the flow path, the fluid rest in the valve portion in the middle of the flow path is not generated, it is possible to prevent the contamination by the reagent in the previous step, it is possible to extract the specific component such as the nucleic acid or the like in the fluid sample at a high purity, and it is possible to analyze precisely.

Figure 10A:
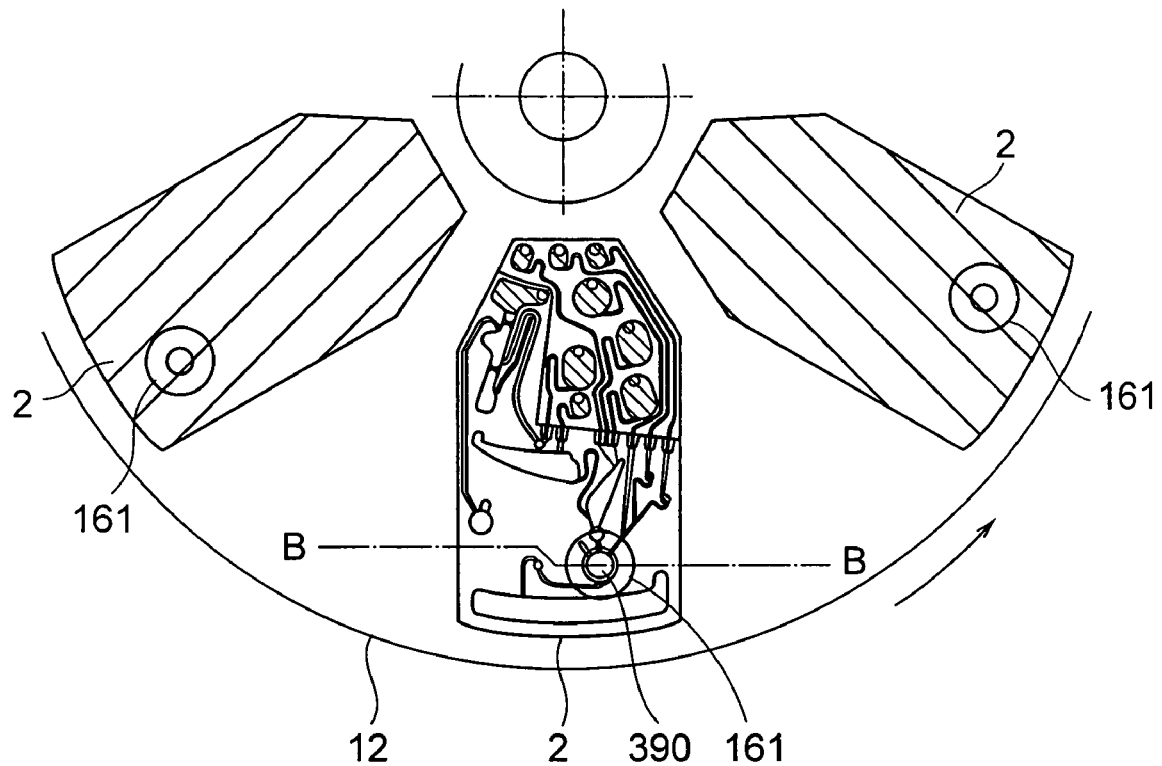
FIGS. 10A and 10B are explanatory views for explaining a second embodiment of the inspection cartridge in accordance with the present invention.
Figure 10B:
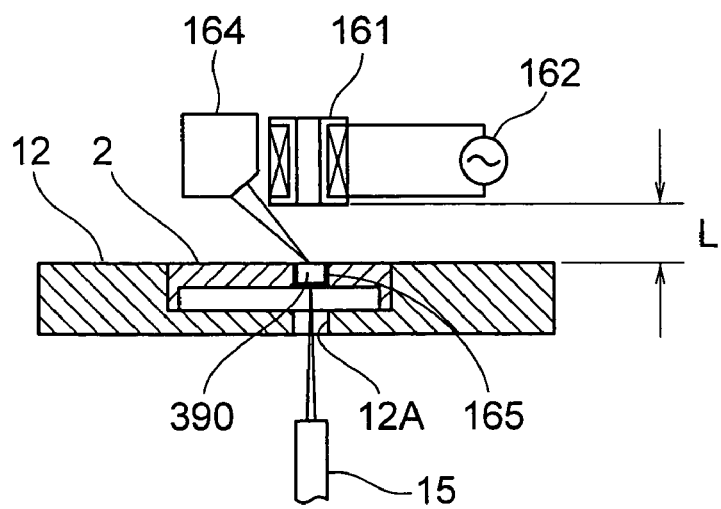

FIGS. 10A and 10B show a second embodiment of the inspection cartridge. In the inspection cartridge in accordance with the present embodiment, a temperature control is executed by using an induction conductive heating method. FIG. 10A shows a state of observing from the above of the retaining disc in which the inspection cartridge in accordance with the present embodiment is retained, and FIG. 10B is a view showing a cross sectional structure along a cut line B-B in FIG. 10A. In the present embodiment, an induction conductive coil 161 and an infrared emission thermometer 164 are arranged in an upper side of the inspection cartridge. A power source 162 is connected to the induction conductive coil 161. The induction conductive coil 161 is supported to the inspection apparatus per the inspection cartridge 2 in accordance with a proper method. For example, a plurality of induction conductive coils 161 may be installed to the inspection apparatus at a predetermined interval above the retaining disc in correspondence to the inspection cartridge 2.

The inspection cartridge 2 is retained within the concave portion of the retaining disc 12. A magnetic material ring 165 is provided along an outer periphery of the eluting fluid recovery container 390 of the inspection cartridge 2. The magnetic material ring 165 may be formed in accordance with a mold forming.

A hole 12A is formed in the retaining disc 12 at a position of the eluting fluid recovery container 390 of the inspection cartridge 2. In order to measure the luminescence amount by the amplification fluid within the eluting fluid recovery container 390 by the inspection apparatus 15 arranged in a lower side of the retaining disc 12, it is desirable that a bottom surface of the eluting fluid recovery container 390 is optically excellent in a flatness and a transparency.

A magnetic field is generated by applying alternating electric current having a high frequency between 20 and 30 kHz to the induction conductive coil 161 from the power source 162, whereby an eddy current is generated in the magnetic material ring 165. If the eddy current flows within the magnetic material ring 165, a heat generation is caused by a joule heat loss. The liquid solution within the eluting fluid recovery container 390 is warmed up on the basis of the heat generation.

A distance between the induction conductive coil 161 and the eluting fluid recovery container 390 is set to L. In the present embodiment, an inner side of the eluting fluid recovery container 390 is heated on the basis of an induction conductive heating between the induction conductive coil 161 and the magnetic material ring 165 which are apart from each other at the distance L. The temperature within the eluting fluid recovery container 390 is measured by the infrared emission thermometer 164. A frequency or a voltage of the alternating electric current applied to the induction conductive coil 161 is controlled on the basis of the measured temperature. Accordingly, the temperature within the eluting fluid recovery container 390 is controlled to a predetermined temperature. In other words, in the present embodiment, a temperature control is executed in a non-contact state with the eluting fluid recovery container 390. Accordingly, even if the retaining disc is under rotation at a high speed or a low speed, the temperature control can be, of course, executed. As a material of the magnetic material ring, a material having a large joule loss due to the eddy current is preferable, and an iron, a stainless steel or the like having a certain degree of electric resistance is preferable rather than a copper family.

Figure 11A:
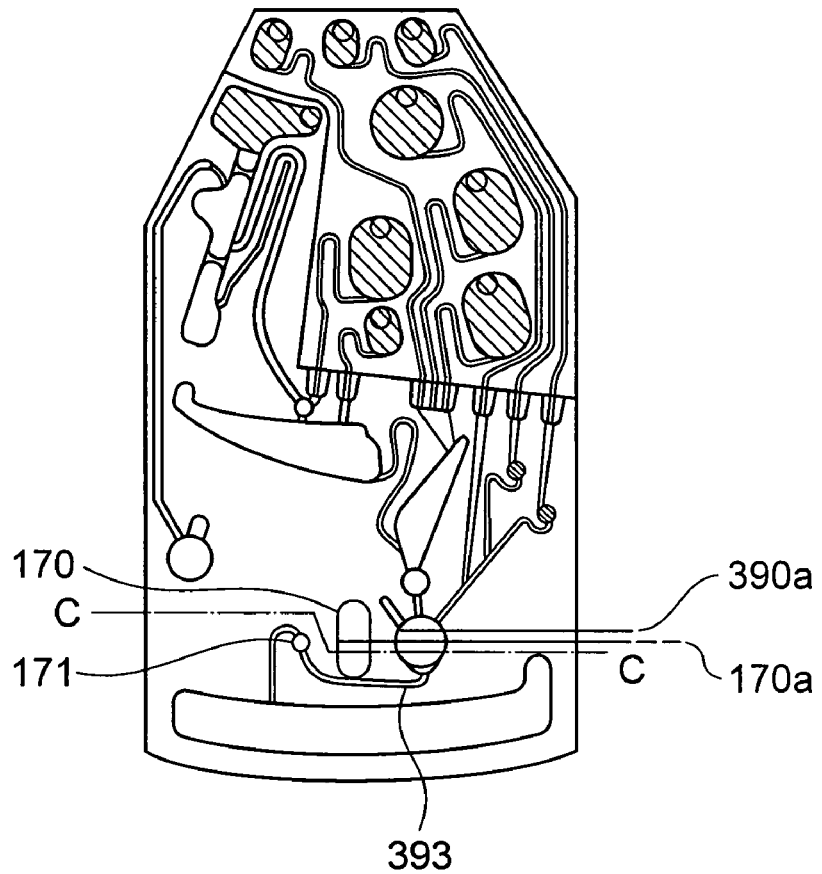
FIGS. 11A and 11B are explanatory views of an operation of a third embodiment of the inspection cartridge in accordance with the present invention.
Figure 11B:
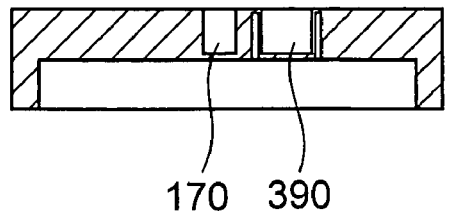

A description will be given of a third embodiment of the inspection cartridge in accordance with the present invention with reference to FIGS. 11 to 13. FIG. 11A shows a planar structure of the inspection cartridge in accordance with the present embodiment. FIG. 11B is a view showing a cross sectional structure of the inspection cartridge along a cut line C-C in FIG. 11A. The inspection cartridge in accordance with the present embodiment is different from the inspection cartridge shown in FIG. 8 in a point that an air reservoir 170 is provided in an inner peripheral side of the waste fluid flow path 393. Further, a capillary tube valve 171 in which a flow path cross section is enlarged is provided in the middle of the waste fluid flow path 393.

Figure 12A:
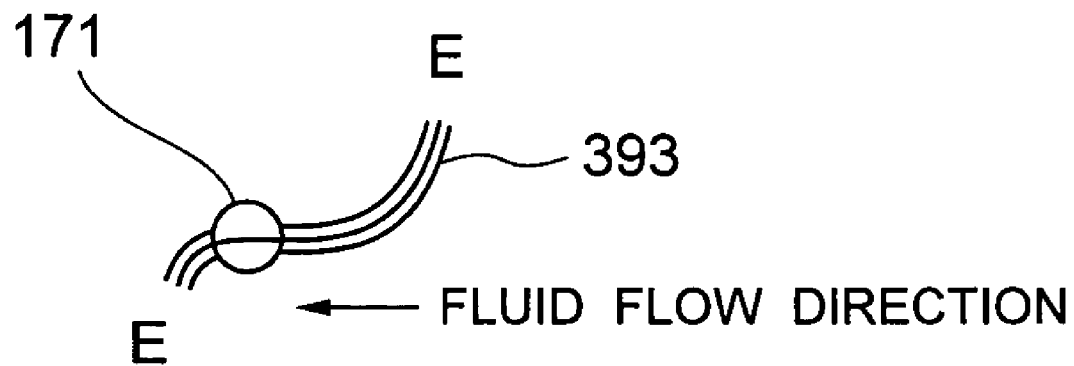
FIGS. 12A and 12B are explanatory views of an operation of a capillary tube valve in the third embodiment of the inspection cartridge in accordance with the present invention.
Figure 12B:
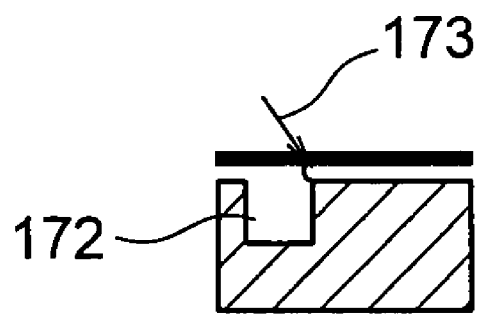

FIGS. 12A and 12B show details of the capillary tube valve 171. FIG. 12A shows a planar structure of the waste fluid flow path 393 including the capillary tube valve 171, and FIG. 12B is a view showing a cross sectional structure of the inspection cartridge along a cut line E-E in FIG. 12A. The capillary tube 171 is structured by a concave portion 172 formed on the path of the waste fluid flow path 393. The concave portion 172 has a flow path cross sectional area which is larger than the flow path cross sectional area of the waste fluid flow path 393. In other words, a width and a depth of the concave portion 172 are larger than a width and a depth of the waste fluid flow path 393.

The liquid solution within the eluting fluid recovery container 390 moves within the waste fluid flow path 393 on the basis of the capillary tube force, and reaches the capillary tube valve 171. However, since a cross sectional area of the flow path becomes large there, the capillary tube force is reduced, and the liquid solution does not move more and stops. Accordingly, a vapor-liquid interface 173 is generated in an inlet of the concave portion 172. The vapor-liquid interface is formed on the basis of a surface tension effect, and is not broken in the case that the pressure from the waste fluid flow path 393 is equal to or less than a fixed value. Therefore, the vapor-liquid interface serves as a kind of valve body preventing the liquid from being fluidized further.

Next, a description will be given of a function of the air reservoir 170. During the rotation of the retaining disc, the eluting fluid within the eluting fluid recovery container 390 is pushed out to an outer side in a radial direction on the basis of the operation of the centrifugal force, and moves into the air reservoir 170 via the waste fluid flow path 393. However, since the air is previously charged within the air reservoir 170, the air is compressed if the eluting fluid moves into the air reservoir 170. When the pressure of the eluting fluid moving into the air reservoir 170 and the pressure of the air balance, the ingression of the eluting fluid is stopped. At this time, the position 170a in the radial direction of the liquid surface level within the eluting fluid recovery container 390 exists in an outer peripheral side of the position 390a in the radial direction of the liquid level within the eluting fluid recovery container 390.

Figure 13A:
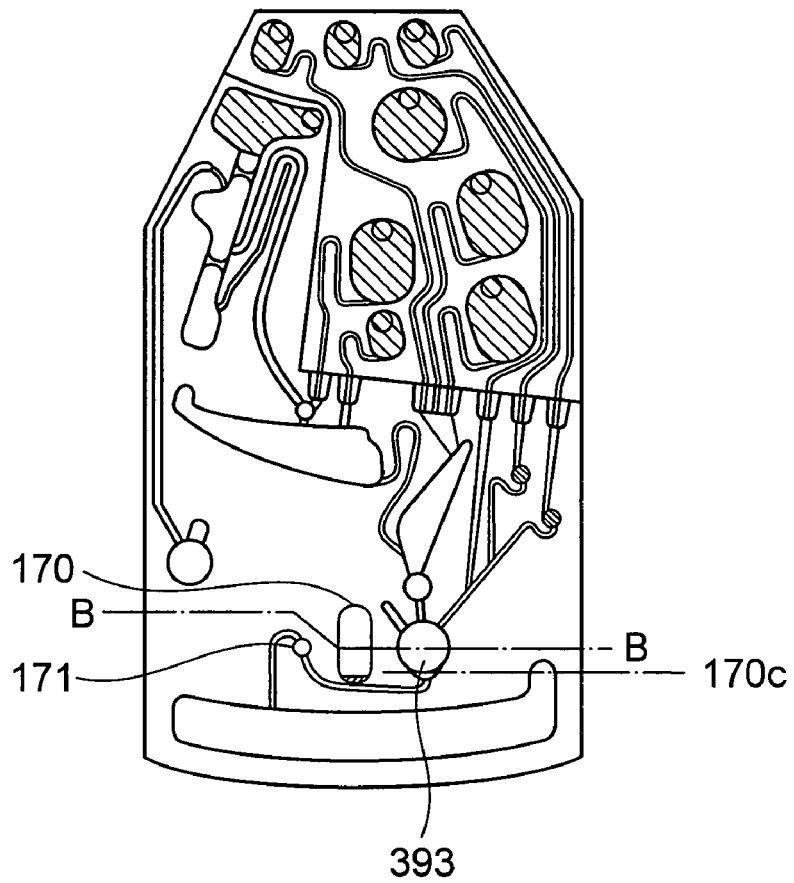
FIGS. 13A and 13B are explanatory views of an operation of the third embodiment of the inspection cartridge in accordance with the present invention.
Figure 13B:
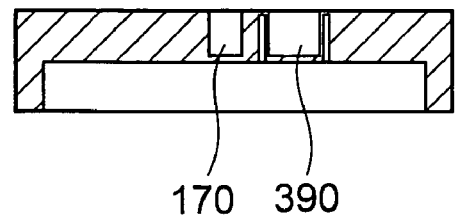

FIGS. 13A and 13B show a state in which the rotation of the retaining disc is stopped. When stopping the rotation of the retaining disc, the centrifugal force is not applied, the balance between the pressure of the eluting fluid and the pressure of the air within the air reservoir 170 is broken. Accordingly, the eluting fluid within the air reservoir 170 is pushed out by the air pressure, and is returned to the eluting fluid recovery container 390. Therefore, the position 170c in the radial direction of the liquid surface level within the air reservoir 170 comes close to the bottom surface of the air reservoir 170. When rotating the retaining disc again, the position in the radial direction of the liquid surface level within the air reservoir 170 moves to the position 170c in FIG. 11A on the basis of the operation of the centrifugal force. As mentioned above, in accordance with the present embodiment, the liquid surface level within the air reservoir 170 is changed by repeating the rotation and the stop of the retaining disc. If the liquid surface level within the air reservoir 170 is changed, the liquid surface level within the eluting fluid recovery container 390 is changed, and the eluting fluid comes and goes between the air reservoir 170 and the eluting fluid recovery container 390. Accordingly, the agitation of the eluting fluid within the eluting fluid recovery container 390 is generated.

As described with reference to FIG. 7, it is possible to generate the agitation within the eluting fluid recovery container 390 by repeating the rotation and the stop of the retaining disc in the amplification step so as to sufficiently mix the inspection reagent and the eluting fluid.

In the present embodiment, the concave portion 172 in which the cross section of the flow path is enlarged is used as the capillary tube valve 171, however, the structure may be made such that a gel material having a high viscosity and generating no inhibition with respect to the gene amplification is charged within the waste fluid flow path 393, or the operation of the capillary tube valve can be replaced by closing the resin flow path in accordance with any method such as heating and dissolving the resin flow path.

Figure 14:
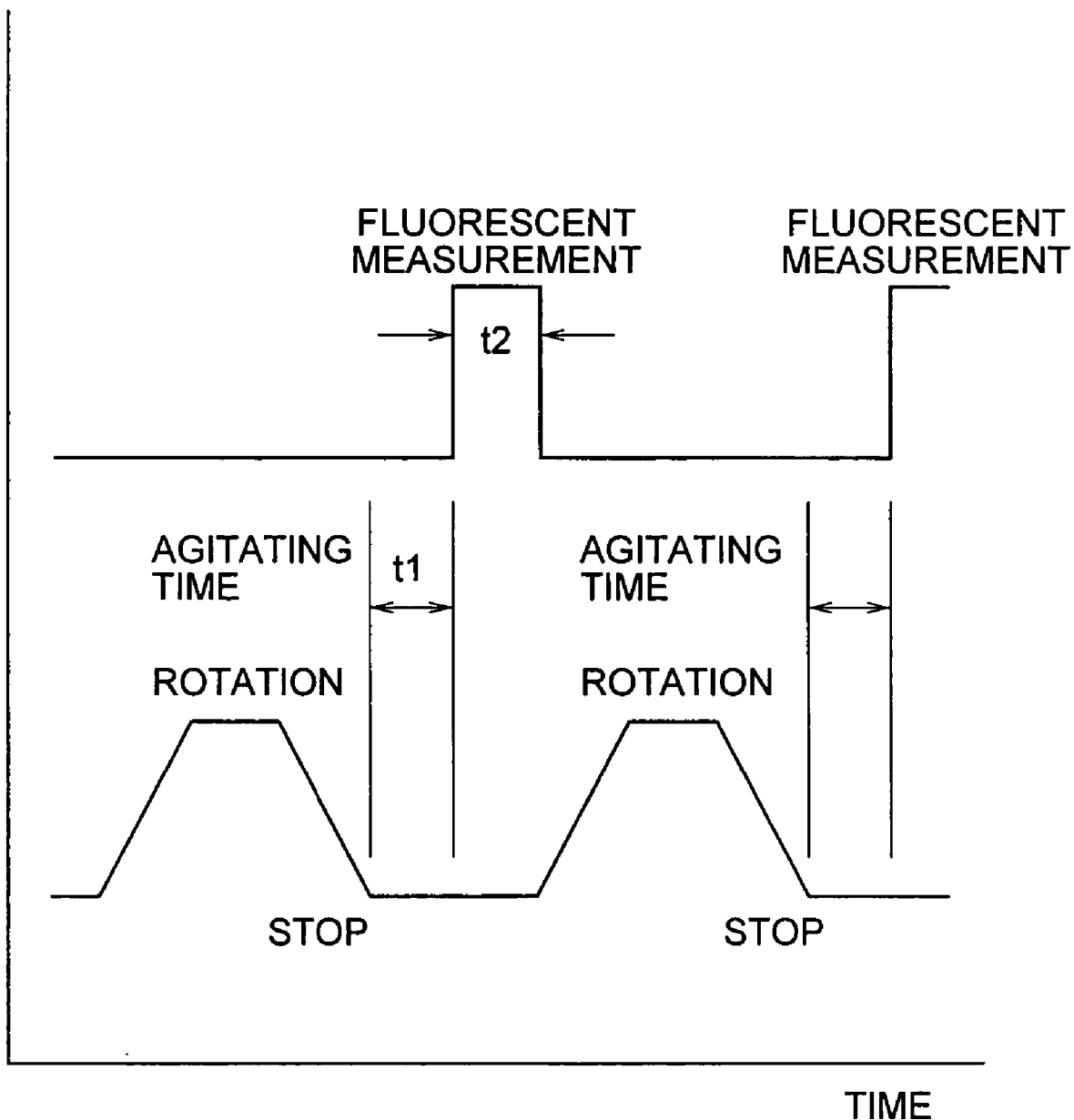
FIG. 14 is an explanatory view for explaining timings of an agitation and a fluorescence measurement in the third embodiment of the inspection cartridge in accordance with the present invention.

Next, a description will be given of a timing of the agitation in the amplification step with reference to FIG. 14. As shown in the drawing, in the amplification step, the rotation and the stop of the retaining disc are repeated. The rotating speed is changed to four states comprising an accelerating time, a fixed speed time, a decelerating time and a stop time. The agitation is executed for a fixed time t1 after the rotation of the retaining disc is stopped, and a fluorescence measurement is thereafter executed at a time t2. In other words, if the decelerating time is finished, the retaining disc is rotated again. In the amplification step, the amplification reaction is promoted and the inspection time can be shortened by agitating while warming up the eluting fluid recovery container 390.

Figure 15A:
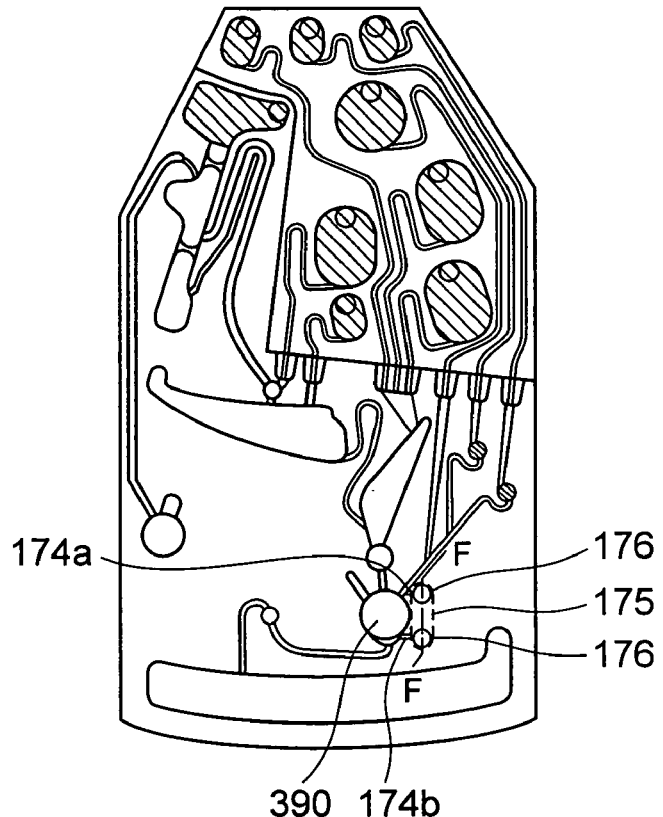
FIGS. 15A and 15B are explanatory views of an operation of a fourth embodiment of the inspection cartridge in accordance with the present invention.
Figure 15B:
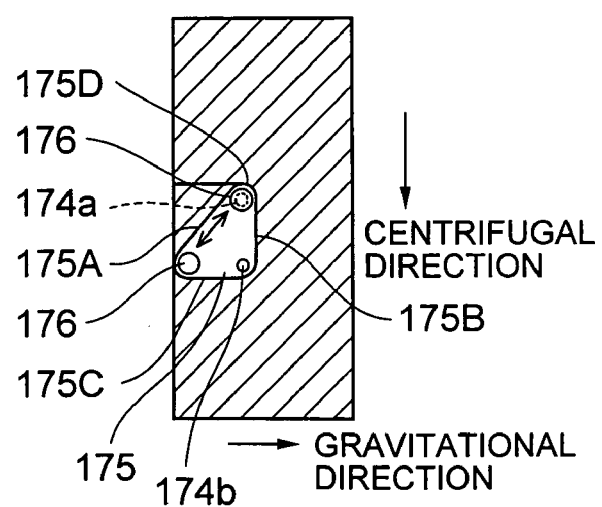

Next, FIGS. 15A and 15B show a fourth embodiment of the inspection cartridge in accordance with the present invention. As shown in FIG. 15A, in the present embodiment, the agitation container 175 extending in the radial direction is provided in adjacent to the eluting fluid recovery container 390 in the base plate. Both ends of the agitation container 175 are connected to the eluting fluid recovery container 390 respectively by the communication flow paths 174a and 174b. Accordingly, the eluting fluid is charged within the agitation container 175. A cross section of the agitation container 175 is formed approximately in a triangular shape. In other words, it is constituted by an upper surface 175A inclined to an upper surface of the base plate, a parallel bottom surface 175B and a vertical outer peripheral side surface 175C. An interval between the upper surface 175A and the bottom surface 175B is enlarged toward an outer peripheral side from an inner peripheral side. A float 176 having a smaller specific gravity than that of the liquid solution within the eluting fluid recovery container 390 is arranged within the agitation container 175.

When the retaining disc is rotated, the eluting fluid having the large specific gravity moves in the direction of the outer peripheral side surface 175C on the basis of the operation of the centrifugal force, and the float 176 having the small specific gravity moves to the inner peripheral side 175D. A gravity and a buoyancy are applied to the float 176 in a direction orthogonal to the applying direction of the centrifugal force, however, an interval between the upper surface 175A and the bottom surface 175B is small in the inner peripheral side 175D of the agitation container 175, and the float 176 can not move in the gravitational direction or the buoyancy direction. Since the float 176 moves to an inner peripheral side from an outer peripheral side on the basis of the operation of the centrifugal force, the liquid solution within the agitation container 175 is pushed out into the eluting fluid recovery container 390 via a communication flow path 174a in an inner peripheral side, and on the contrary, the liquid solution within the eluting fluid recovery container 390 flows into the agitation container 175 via a communication flow path 174b in an outer peripheral side.

When the rotation of the retaining is stopped, the centrifugal force is not applied, however, the gravity and the buoyancy are applied. Since the specific gravity of the float 176 is small, the buoyancy is larger than the gravity. Accordingly, a force in an upward direction on the basis of the buoyancy is applied to the float 176. Therefore, the float 176 moves along an incline of the upper surface 175A, and moves to the outer peripheral side surface 175C. Since the float 176 moves to the outer peripheral side from the inner peripheral side, the liquid solution within the agitation container 175 is pushed out into the eluting fluid recovery container 390 via the communication flow path 174b in the outer peripheral side, and on the contrary, the liquid solution within the eluting fluid recovery container 390 flows into the agitation container 175 via the communication flow path 174a in the inner peripheral side.

When the rotation and the stop of the retaining disc are repeated, the float 176 moves between the inner peripheral side and the outer peripheral side. Accordingly, the liquid solution goes and comes between the eluting fluid recovery container 390 and the agitation container 175 via the communication flow paths 174a and 174b. Accordingly, the liquid solution within the eluting fluid recovery container 390 is agitated.

Figure 16A:
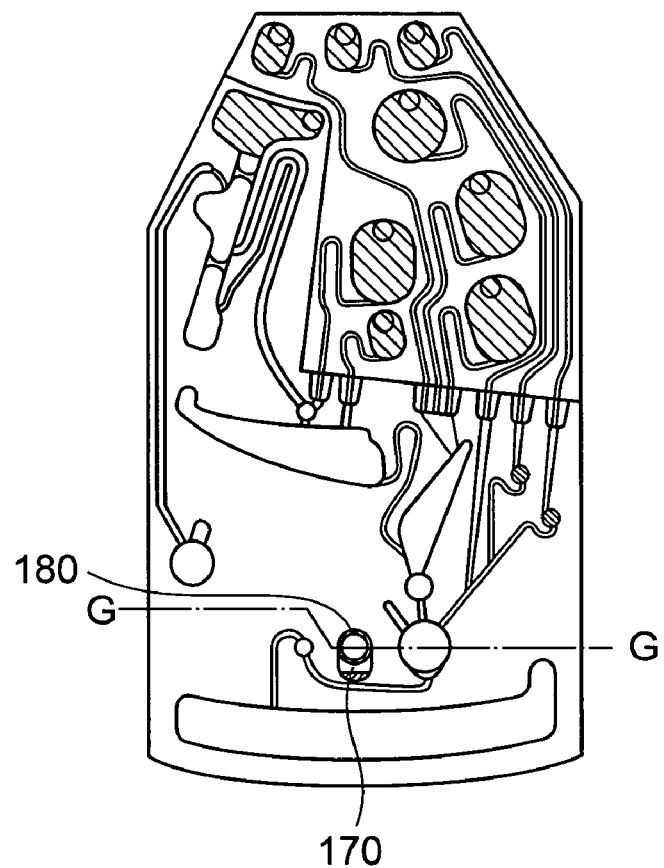
FIGS. 16A and 16B are explanatory views of an operation of a fifth embodiment of the inspection cartridge in accordance with the present invention.
Figure 16B:
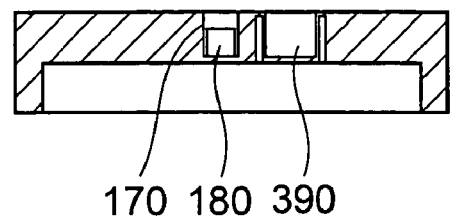

Next, FIGS. 16A and 16B show a fifth embodiment of the inspection cartridge in accordance with the present invention. As shown in FIG. 16A, the air reservoir 170 is provided in the inner peripheral side of the waste fluid flow path 393, and an electric heater 180 is provided within the air reservoir 170. FIG. 16B shows a cross sectional structure along a line G-G in FIG. 16A. An air within the air reservoir 170 is expanded by exciting an electric heater 180. The liquid solution within the air reservoir 170 is pushed out on the basis of the expansion of the air within the air reservoir 170 so as to move into the eluting fluid recovery container 390. The air within the air reservoir 170 is contracted by stopping the excitation of the electric heater 180. The liquid solution within the eluting fluid recovery container 390 moves into the air reservoir 170 on the basis of the contraction of the air within the air reservoir 170. Accordingly, the liquid solution goes and comes between the eluting fluid recovery container 390 and the air reservoir 170 by repeating the expansion and the contraction of the air within the air reservoir 170, by means of the electric heater 180. Therefore, the agitation of the liquid solution is executed within the eluting fluid recovery container 390.

A Peltier element may be installed in addition to the electric heater 180. The contraction of the air can be promoted by stopping the excitation of the electric heater 180 and exciting the Peltier element.

Figure 17A:
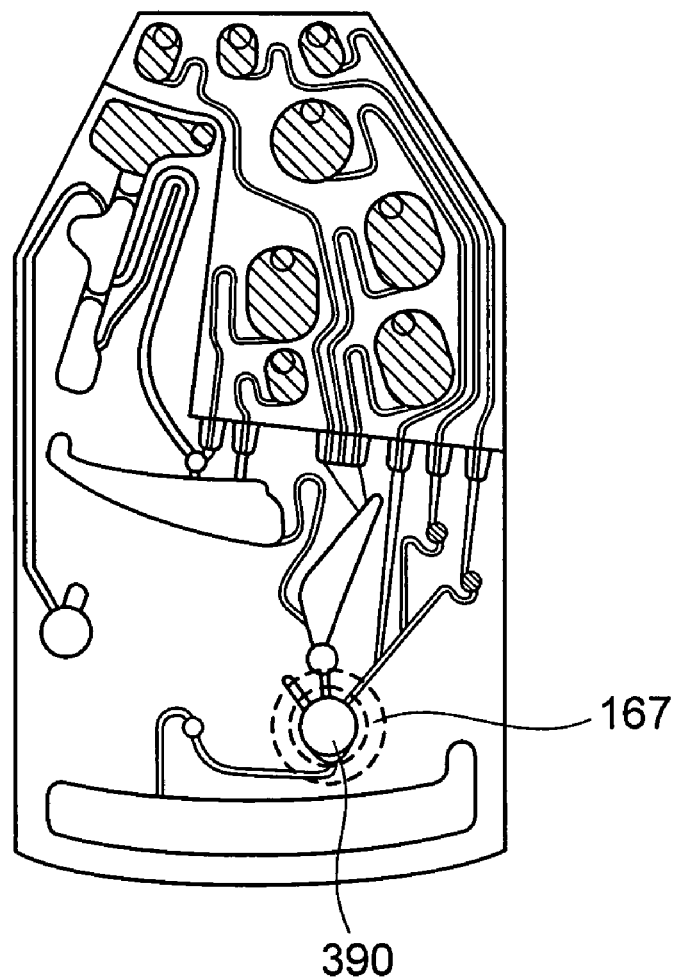
FIGS. 17A and 17B are explanatory views of an operation of a sixth embodiment of the inspection cartridge in accordance with the present invention.
Figure 17B:

Next, FIGS. 17A and 17B show a sixth embodiment of the inspection cartridge in accordance with the present invention. As shown in FIG. 17A, in the inspection cartridge in accordance with the present embodiment, a ring-shaped agitation container 167 is formed in such a manner as to surround the eluting fluid recovery container 390. A magnetic material ring 165 shown in FIG. 17B is arranged within the agitation container 167.

Figure 18A:
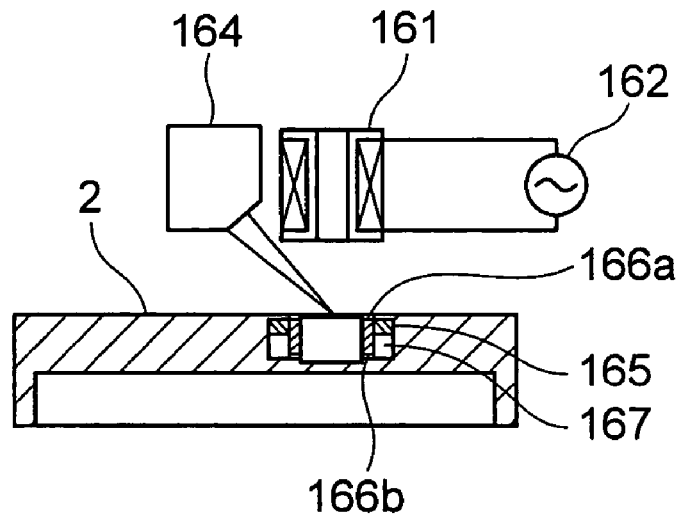
FIGS. 18A and 18B are explanatory views of an operation of the sixth embodiment of the inspection cartridge in accordance with the present invention.
Figure 18B:
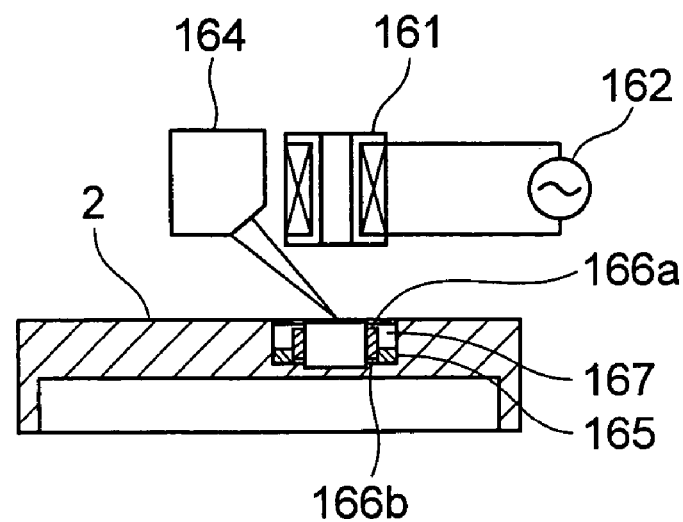

As shown in FIGS. 18A and 18B, the eluting fluid recovery container 390 and the agitation container 167 are communicated in an upper side communication flow path 166a and a lower side communication flow path 166b. Accordingly, the eluting fluid is filled within the agitation container 167. The induction conductive coil 161 and the infrared emission thermometer 164 are arranged in an upper side of the inspection cartridge. The power source 162 is connected to the induction conductive coil 161. The induction conductive coil 161 may be structured such as to be supported in accordance with a proper method per the inspection cartridge 2, and be rotated together with the retaining disc. FIG. 18A shows a state in which the induction conductive coil 161 is excited. When applying a low-frequency alternating electric current or direct current to the induction conductive coil 161, the magnetic field is generated. The magnetic material ring 165 is exposed to a force in an upward direction on the basis of the magnetic field. Since a magnitude of the force in the upward direction on the basis of the magnetic field is sufficiently large in comparison with the weight of the magnetic material ring 165, the magnetic material ring 165 moves upward within the agitation container 167. The eluting fluid recovery container 390 and the agitation container 167 are covered by the cartridge cover 32, the magnetic material ring 165 does not jump out from the agitation container 167.

If the magnetic material ring 165 moves upward within the agitation container 167, the liquid solution within the agitation container 167 is pushed out by the magnetic material ring 165, and moves into the eluting fluid recovery container 390 via the upper communication flow path 166a, and the liquid solution within the eluting fluid recovery container 390 is introduced into the agitation container 167 via the lower communication flow path 166b.

FIG. 18B shows a state in which the excitation of the induction conductive coil 161 is disconnected. The magnetic material ring 165 moves downward within the agitation container 167 on the basis of the gravity. When the magnetic material ring 165 moves downward within the agitation container 167, the liquid solution within the agitation container 167 is pushed out by the magnetic material ring 165, and moves into the eluting fluid recovery container 390 via the lower communication flow path 166b, and the liquid solution within the eluting fluid recovery container 390 is introduced into the agitation container 167 via the upper communication flow path 166a.

As mentioned above, in accordance with the present embodiment, the magnetic material ring 165 reciprocates in the vertical direction within the agitation container 167 by repeating the excitation of the induction conductive coil 161 and the disconnection of the excitation. Accordingly, the liquid solution goes and comes between the eluting fluid recovery container 390 and the agitation container 167, and the liquid solution within the eluting fluid recovery container 390 is agitated.

In this case, as described with reference to FIGS. 10A and 10B, the structure may be made such that the eddy current is generated in the magnetic material ring 165 by applying the alternating electric current having the high frequency between 20 to 30 kHz to the induction conductive coil 161, thereby heating the liquid solution within the eluting fluid recovery container 390. Therefore, the magnetic material ring 16 can be functioned as the heating heater as well as being used as the agitating element. In the amplification step, it is necessary to simultaneously execute the agitation and the heating. Accordingly, the magnetic material ring 165 in accordance with the present embodiment is preferable in the case of executing the agitation and the heating in the amplification step. Therefore, it is possible to reduce a number of the used parts as well as it is possible to reduce a number of operating process.

Since the magnetic material ring 165 is brought into direct contact with the fluid within the eluting fluid recovery container 390, it is necessary to coat the magnetic material ring 165 with a material which does not affect the gene amplification, for example, a fluorine contained resin or the like.

Figure 19A:
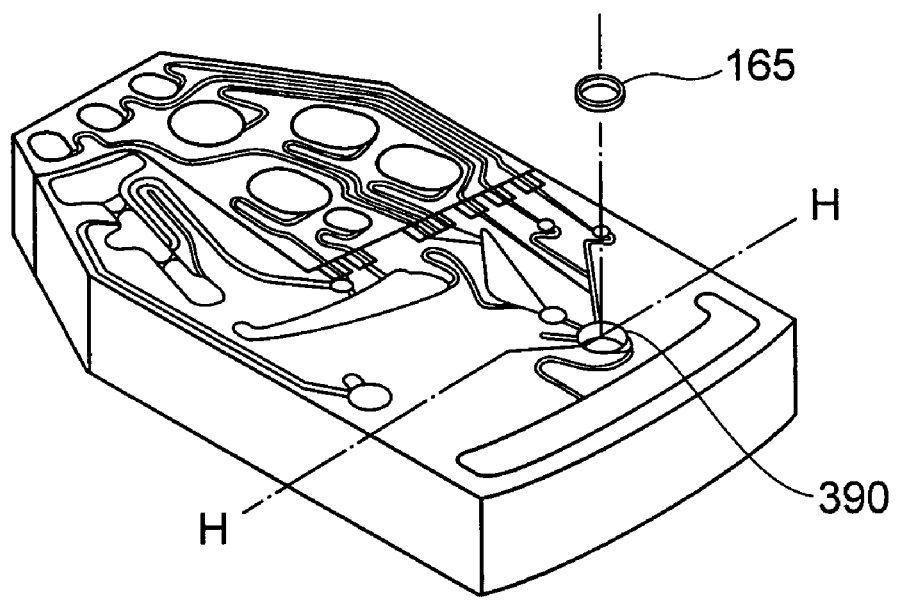
FIGS. 19A and 19B are explanatory views of an operation of a seventh embodiment of the inspection cartridge in accordance with the present invention.
Figure 19B:
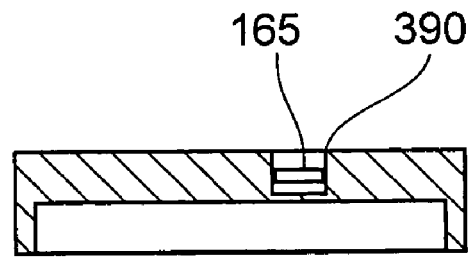

FIGS. 19A and 19B show a seventh embodiment of the inspection cartridge in accordance with the present invention. As shown in FIG. 19A, in the inspection cartridge in accordance with the present embodiment, the magnetic material ring 165 is directly inserted to the eluting fluid recovery container 390. FIG. 16B shows a cross sectional structure of the eluting fluid recovery container 390 and the magnetic material ring 165 arranged therein. In FIG. 19B, an illustration of the induction conductive coil 161 and the infrared emission thermometer 164 provided in the upper side of the inspection cartridge is omitted. The magnetic material ring 165 reciprocates in the vertical direction within the eluting fluid recovery container 390 by repeating the excitation of the induction conductive coil 161 and the disconnection of the excitation. Accordingly, the liquid solution within the eluting fluid recovery container 390 is agitated. In the case of the present embodiment, the agitation and the heating may be simultaneously executed by the magnetic material ring 165. In the present embodiment, it is possible to achieve both of the agitation and the heating while the structure is simple.

Figure 20A:
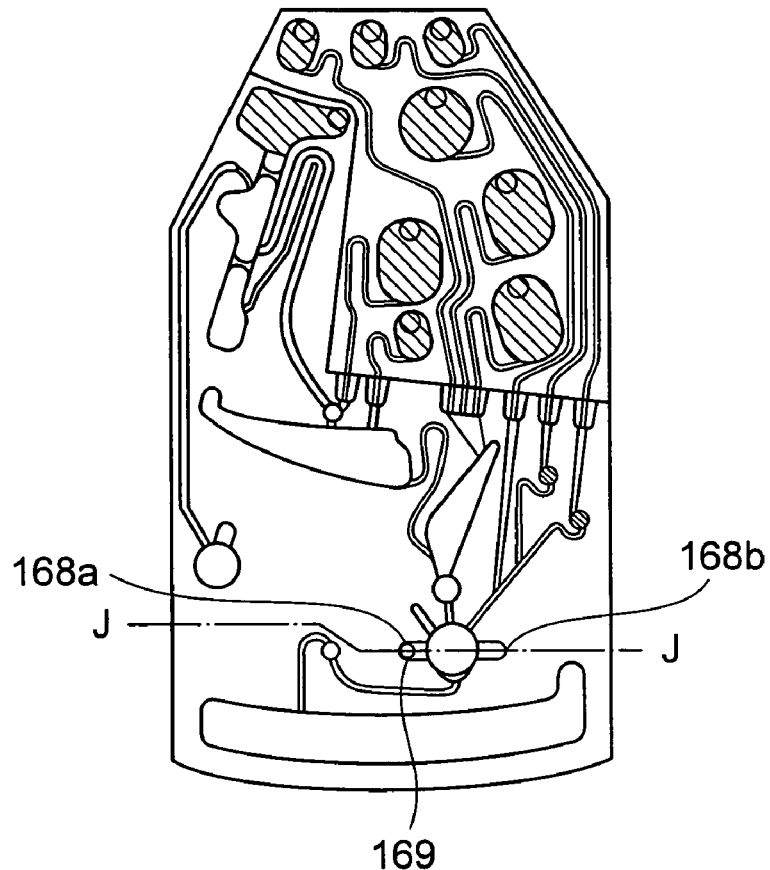
FIGS. 20A and 20B are explanatory views of an operation of an eighth embodiment of the inspection cartridge in accordance with the present invention.
Figure 20B:
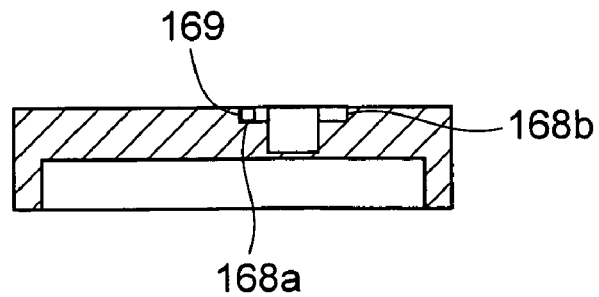

FIGS. 20 and 21 show an eighth embodiment of the inspection cartridge in accordance with the present invention. In the present embodiment, both sides of the eluting fluid recovery container 390 are provided with agitating flow paths 168a and 168b extending in a tangential direction of the retaining disc, and a magnetic material ball 169 is arranged with the flow path. The agitating flow paths 168a and 168b are connected to the eluting fluid recovery container 390. Accordingly, the eluting fluid is filled in the agitating flow paths 168a and 168b. The agitating flow paths 168a and 168b correspond to shallower grooves than the eluting fluid recovery container 390.

Figure 21A:
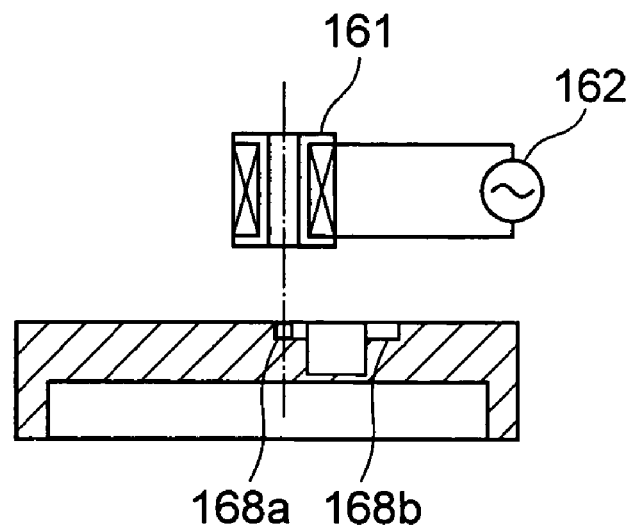
FIGS. 21A and 21B are explanatory views of an operation of the eighth embodiment of the inspection cartridge in accordance with the present invention.
Figure 21B:
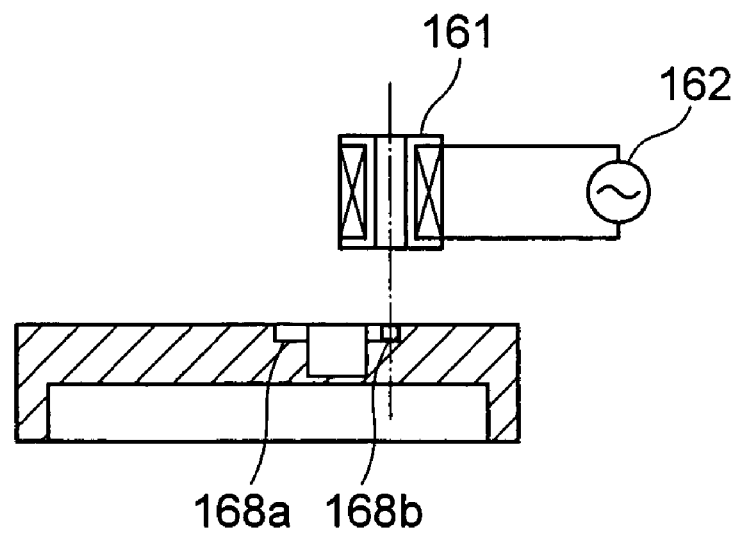

A description will be given with reference to FIGS. 21A and 21B. The induction conductive coil 161 is provided in an upper side of the inspection cartridge. The induction conductive coil 161 is connected to the power source 162. In the present embodiment, the inspection cartridge is moved in a radial direction in a state in which the magnetic field is generated by applying the low-frequency alternating electric current or direct electric current to the induction conductive coil 161. FIG. 21A shows a state in which the inspection cartridge is arranged in such a manner that a center of the induction conductive coil 161 aligns with a position of an outer end portion of one agitating flow path 168*a*. FIG. 21B shows a state in which the inspection cartridge is arranged in such a manner that the center of the induction conductive coil 161 aligns with a position of an outer end portion of the other agitating flow path 168*b*. The magnetic material ball 169 is attracted by the magnetic field generated by the induction conductive coil 161. Since the eluting fluid recovery container 390 and the agitating flow paths 168*a* and 168*b* are covered by the cartridge cover 32, the magnetic material ball 169 does not jump out from the eluting fluid recovery container 390 and the agitating flow paths 168*a* and 168*b*.

As shown in FIG. 21A, in the case that the center of the induction conductive coil 161 exists at the position of the outer end portion of the one agitating flow path 168*a*, the magnetic material ball 169 is arranged in the outer end portion of the one agitating flow path 168*a*. As shown in FIG. 21B, in the case that the center of the induction conductive coil 161 exists at the position of the outer end portion of the other agitating flow path 168*b*, the magnetic material ball 169 is arranged in the outer end portion of the other agitating flow path 168*a*.

As mentioned above, in accordance with the present embodiment, the magnetic material ball 169 reciprocates along two agitating flow paths 168*a* and 168*b* by reciprocating the inspection cartridge in the radial direction. Accordingly, the eluting fluid within the eluting fluid recovery container 390 is agitated. In the case of executing the fluorescence measurement, the magnetic material ball 169 is arranged in the end portion of one of two agitating flow paths 168*a* and 168*b*, so that the magnetic material ball 169 does not prevent the fluorescence measurement.

Figure 22:
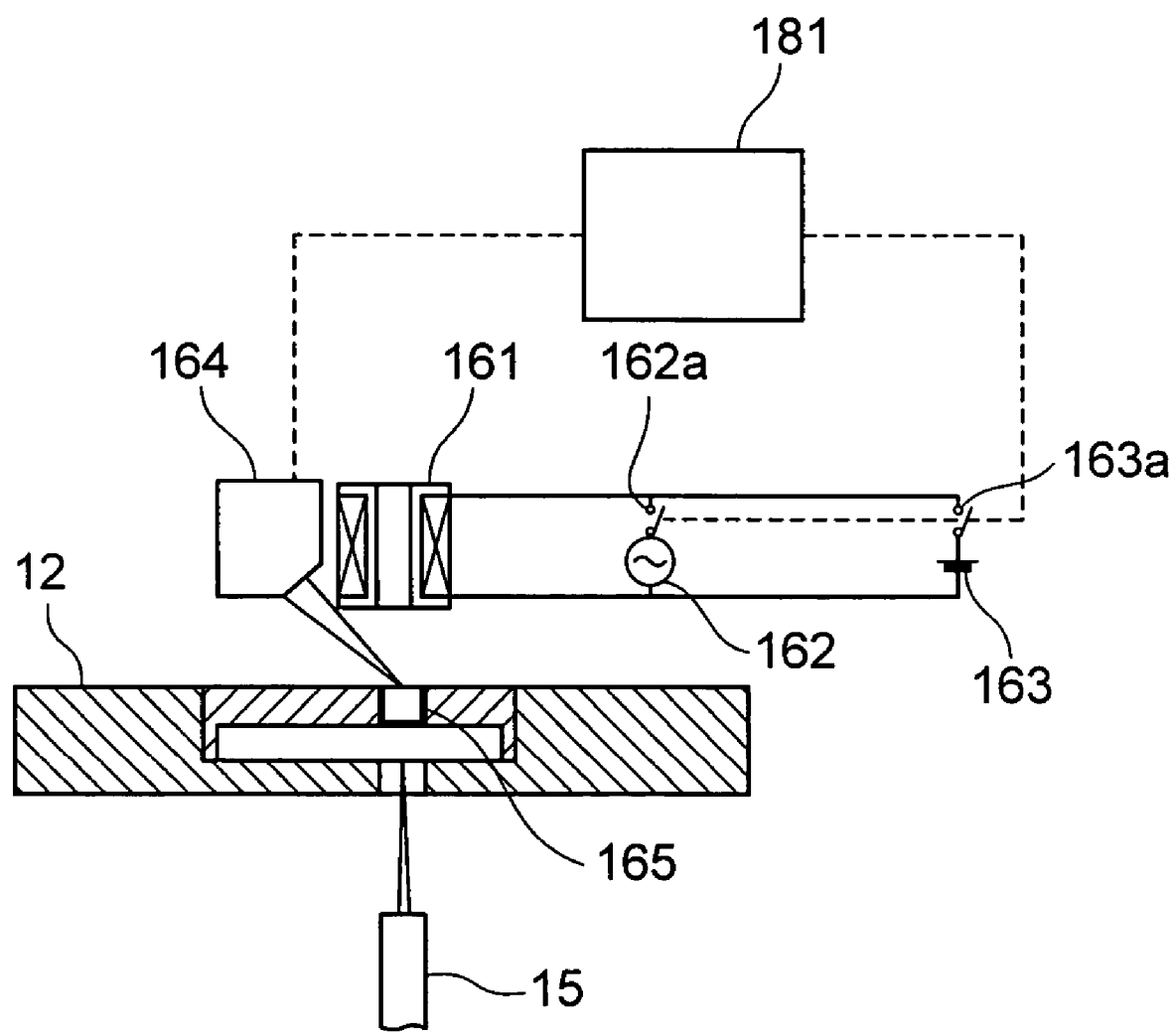
FIG. 22 is a view for explaining an apparatus for switching an agitation and a warming, in the eighth embodiment of the inspection cartridge in accordance with the present invention.

FIG. 22 shows an example of the power source apparatus supplying the power to the induction conductive coil. In the example mentioned above, the direct electric current is supplied to the induction conductive coil at a time of agitating, and the low-frequency alternating electric current is supplied to the induction conductive coil in the case of the induction conductive heating. In other words, in the case that the agitation and the heating are switched, it is necessary to switch the power source. In the present embodiment, a control apparatus 181 for switching the power source is provided. A switch 162*a* is connected to the alternating current power source, and a switch 163*a* is connected to the direct current power source 163. The control apparatus 181 supplies a command for turning on the switch 163*a* and turning off the switch 162*a* at a time of agitating. The control apparatus 181 supplies a command for turning off the switch 163*a* and turning on the switch 162*a* at a time of heating. The control apparatus 181 inputs a temperature signal from the infrared emission thermometer 164 so as to execute a warming control.

It should be further understood by those skilled in the art that although the foregoing description has been made on embodiments of the invention, the invention is not limited thereto and various changes and modifications may be made without departing from the spirit of the invention and the scope of the appended claims.

The invention claimed is:

1. A chemical analysis apparatus comprising:

a retaining disc rotatable around a rotating axis passing through a center;

a detachable inspection cartridge retained in said retaining disc;

said inspection cartridge having a base plate including a container and a flow path formed by a concave portion, and a cover covering said container and said flow path; and a liquid solution being moved to the container in an outer peripheral side with respect to said rotating axis from the container in an inner peripheral side with respect to said rotating axis via said flow path, by utilizing a centrifugal force generated by a rotation of said retaining disc, wherein the chemical analysis apparatus is provided with an agitating means for agitating the liquid solution within said container, and a waste fluid storage container storing a waste fluid, wherein said agitating means has an air reservoir container connected to a flow path connected to an outlet of said container, the liquid solution within said container moves into said air reservoir container at a time when a centrifugal force is applied, and the liquid solution moving into said air reservoir container is returned to said container at a time when the centrifugal force is not applied, and wherein said air reservoir container is provided on an inner peripheral side of a waste fluid flow path between said container and said waste fluid storage container.

2. A chemical analysis apparatus as claimed in claim 1, wherein a warming means for warming up the water solution within said container is provided.

3. A chemical analysis apparatus as claimed in claim 2, wherein said warming means has a magnetic material arranged within said container and a coil provided apart from said inspection cartridge, an eddy current is generated within said magnetic material by supplying a high-frequency alternating electric current to said coil, and the water solution within said container is warmed up by said eddy current.

4. A chemical analysis apparatus as claimed in claim 2, wherein said chemical analysis apparatus has a magnetic material arranged within said container, a coil provided apart from said inspection cartridge and a power source apparatus supplying a power to said coil, and said power source apparatus supplies a direct current to said coil in the case that said magnetic material is used as the agitating means, and supplies a high-frequency alternating current to said coil in the case that said magnetic material is used as the warming means.

5. A chemical analysis apparatus as claimed in claim 2, wherein said base plate is provided with a sample container accommodating a sample, a capture portion for capturing a specific material contained in said sample, an eluting fluid container retaining an eluting fluid for eluting said material captured by said capture portion, an eluting fluid recovery container accommodating the eluting fluid containing said material discharged from said capture portion, a detection reagent container for retaining a detection reagent for detecting said material from the eluting fluid containing said material accommodated in said eluting fluid recovery container, and a waste fluid storage container recovering a water solution discharged via said capture portion and said eluting fluid recovery container, and said warming means is provided in said eluting fluid recovery container.

6. A chemical analysis cartridge comprising:
a base plate having a container and a flow path formed by a concave portion;
a cover covering said container and said flow path; and
a liquid solution being moved to the container in an outer peripheral side with respect to a rotating axis perpendicular to said base plate from the container in an inner peripheral side with respect to said rotating axis via said flow path, by utilizing a centrifugal force generated by a rotation around said rotating axis,
wherein chemical analysis cartridge is provided with an agitating means for agitating the liquid solution within said container, and a waste fluid storage container storing a waste fluid,
wherein said agitating means has an air reservoir container connected to a flow path connected to an outlet of said container, the liquid solution within said container moves into said air reservoir container at a time when a centrifugal force is applied, and the liquid solution moving into said air reservoir container is returned to said container at a time when the centrifugal force is not applied, and
wherein said air reservoir container is provided on an inner peripheral side of a waste fluid flow path between said container and said waste fluid storage container.

7. A chemical analysis cartridge as claimed in claim 6, wherein a warming means for warming up the water solution within said container is provided.

8. A chemical analysis cartridge as claimed in claim 7, wherein said warming means has a magnetic material arranged within said container, an eddy current is generated within said magnetic material by supplying a high-frequency alternating electric current to a coil provided apart from said inspection cartridge, and the water solution within said container is warmed up by said eddy current.

9. A chemical analysis cartridge as claimed in claim 7, wherein said base plate is provided with a sample container accommodating a sample, a capture portion for capturing a specific material contained in said sample, an eluting fluid container accommodating an eluting fluid for eluting said material captured by said capture portion, an eluting fluid recovery container accommodating the eluting fluid containing said material discharged from said capture portion, a detection container for retaining the eluting fluid containing said material from said eluting fluid recovery container for detecting said material, and a waste fluid storage container recovering a water solution discharged via said capture portion and said eluting fluid recovery container, and said warming means is provided in said eluting fluid recovery container.

10. A chemical analysis cartridge for use in a chemical analysis apparatus having a retaining disc rotatable around a rotating axis, the chemical analysis cartridge having an inner peripheral side adapted to face towards the rotating axis of the retaining disc of the chemical analysis apparatus and an outer peripheral side adapted to face away from the rotating axis of the retaining disc of the chemical analysis apparatus, and comprising:
a base plate having an eluting fluid recovery container, a waste fluid storage container for storing a waste fluid and a waste fluid flow path formed by a concave portion connecting the eluting fluid recovery container and the waste fluid storage container;
a cover covering the eluting fluid recovery container, the waste fluid storage container and the waste fluid flow path,
wherein a liquid eluting solution is moved in the eluting fluid recovery container from the inner peripheral side of the eluting fluid recovery container to the outer peripheral side of the eluting fluid recovery container by utilizing a centrifugal force generated by rotation of the chemical analysis cartridge around the rotating axis; and
agitating means comprising an air reservoir container connected to an inner peripheral side of the waste fluid flow path between the eluting fluid recovery container and the waste fluid storage container, and configured such that the liquid eluting solution within the eluting fluid recovery container moves into the air reservoir container at a time when a centrifugal force is applied, and the liquid eluting solution within the air reservoir chamber is returned to the eluting fluid recovery container at a time when the centrifugal force is not applied.

11. A chemical analysis apparatus comprising:
a retaining disc rotatable around a rotating axis; and
the chemical analysis cartridge according to claim 10 retained in the retaining disc.

* * * * *